United States Patent
Wu et al.

(10) Patent No.: US 6,562,991 B1
(45) Date of Patent: May 13, 2003

(54) GELATINOUS COMPOSITIONS FORMED FROM HYDROXYALUMINOXANE, SOLID COMPOSITIONS FORMED THEREFROM, AND THE USE OF SUCH COMPOSITIONS AS CATALYST COMPONENTS

(75) Inventors: Feng-Jung Wu, Baton Rouge, LA (US); Larry S. Simeral, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 10/170,166

(22) Filed: Jun. 11, 2002

Related U.S. Application Data

(60) Division of application No. 09/946,976, filed on Sep. 5, 2001, now Pat. No. 6,492,292, which is a continuation-in-part of application No. 09/655,218, filed on Sep. 5, 2000, now Pat. No. 6,462,212, which is a continuation-in-part of application No. 09/177,736, filed on Oct. 23, 1998, now Pat. No. 6,160,145.

(51) Int. Cl.[7] .................................................. C07F 5/06

(52) U.S. Cl. ........................................ 556/182; 556/179

(58) Field of Search ................................. 556/179, 182

(56) References Cited

U.S. PATENT DOCUMENTS

| | | | |
|---|---|---|---|
| 3,300,458 A | 1/1967 | Manyik et al. | 260/88.2 |
| 4,658,078 A | 4/1987 | Slaugh et al. | 585/512 |
| 4,752,597 A | 6/1988 | Turner | 502/104 |
| 4,814,540 A | 3/1989 | Watanabe et al. | 585/523 |
| 4,960,878 A | 10/1990 | Crapo et al. | 556/179 |
| 5,008,228 A | 4/1991 | Chang | 502/111 |
| 5,041,584 A | 8/1991 | Crapo et al. | 556/179 |
| 5,087,788 A | 2/1992 | Wu | 585/512 |
| 5,126,303 A | 6/1992 | Resconi et al. | 502/117 |
| 5,145,819 A | 9/1992 | Winter et al. | 502/117 |
| 5,147,949 A | 9/1992 | Chang | 526/129 |
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,296,433 A | 3/1994 | Siedle et al. | 502/117 |
| 5,321,107 A | 6/1994 | Tsutsui et al. | 526/138 |
| 5,324,800 A | 6/1994 | Welborn, Jr. et al. | 526/160 |
| 5,340,786 A | 8/1994 | Tsutsui et al. | 502/117 |
| 5,374,753 A | 12/1994 | Yamada et al. | 556/11 |
| 5,384,299 A | 1/1995 | Turner et al. | 502/155 |
| 5,391,629 A | 2/1995 | Turner et al. | 525/268 |
| 5,408,017 A | 4/1995 | Turner et al. | 526/134 |
| 5,502,017 A | 3/1996 | Marks et al. | 502/103 |
| 5,539,068 A | 7/1996 | Devore et al. | 526/126 |
| 5,565,533 A | 10/1996 | Galimberti et al. | 526/127 |
| 5,599,761 A | 2/1997 | Turner | 502/152 |
| 5,621,126 A | 4/1997 | Canich et al. | 556/9 |
| 5,693,727 A | 12/1997 | Goode et al. | 526/86 |
| 5,712,352 A | 1/1998 | Brant et al. | 526/68 |
| 5,854,166 A | 12/1998 | Marks et al. | 502/153 |

FOREIGN PATENT DOCUMENTS

| | | |
|---|---|---|
| DE | 2608863 | 9/1977 |
| DE | 2608933 | 9/1977 |
| DE | 3240382 | 5/1984 |
| EP | 0277003 | 8/1988 |
| EP | 0277004 | 8/1988 |
| EP | 0816399 | 7/1998 |
| FR | 2010468 | 2/1970 |
| WO | 9602580 | 2/1996 |
| WO | 9832776 | 7/1998 |
| WO | 0024787 | 5/2000 |
| WO | 0132721 | 5/2001 |
| WO | 0132722 | 5/2001 |

OTHER PUBLICATIONS

Bochmann, Manfred "Cationic Group 4 metallocene complexes and their role in polymerisation catalysis: the chemistry of well defined Ziegler catalysts", J. of the Chem. Soc.,Dalton Trans., 1996, vol. 3., pp. 255–270.

Boleslawski, M. et al., "Investigations of The Hydrolysis Reaction Mechanism of Organoaluminium Compounds. $^1$H NMR Spectroscopic Studies on the $R_3Al/H_2O$ Reaction In Polar Solvents", Journal of Organometallic Chem. vol. 255, 1983, pp. 269–278.

Harlan Jeff C. et al., "tert–Butylaluminum Hydroxides and Oxides: Structural Relationship between Alkylalumoxanes and Alumina Gels", Organometallics vol. 13, 1994, pp. 2957–2969.

Harlan et al., "Three–Coordinate Aluminum Is Not a Prerequisite for Catalytic Activity in the Zirconocene–Alumoxane Polymerization of Ethylene" J. Am. Chem. Soc. 1995, vol. 117, pp. 6465–6474.

Jia et al., "Protected (Fluoroaryl)borates as Effective Counteranions for Cationic Metallocene Polymerization Catalysts", Organometallics 1995 vol. 14, pp. 3135–3137.

Johnson et al., "New Pd(II)– and Ni(II)–Based Catalysts for Polymerization of Ethylene and α–Olefins", J. Am. Chem. Soc. 1995, vol. 117, pp. 6414–6415.

Kaminsky, Dr. W., "Metallocene Catalysts", SP'92–Polyethylene World Congress, Dec. 1992, 12 pages.

Killian et al., "Living Polymerization of α–Olefins Using $Ni^{11}$–α–Diimine Catalysts. Synthesis of New Block Polymers Based on α–Olefins", J. Am. Chem. Soc. 1996, vol. 118, pp. 11664–11665.

(List continued on next page.)

Primary Examiner—Caixia Lu
(74) Attorney, Agent, or Firm—Philip M. Pippenger

(57) ABSTRACT

Gelatinous compositions of matter which are useful as polymerization catalyst components and are highly stable in terms of OH-decay rate, as well as similarly stable solid compositions of matter formed from such gelatinous compositions, are described. The gelatinous and solid compositions are formed from hydroxyaluminoxane. Also disclosed is a process comprising converting a hydroxyaluminoxane into a gelatinous composition of matter, whereby the rate of OH-decay for the composition is reduced as compared to that of the hydroxyaluminoxane. Olefin polymerization processes and catalysts formed from these novel compositions of matter also are disclosed.

19 Claims, 9 Drawing Sheets

OTHER PUBLICATIONS

Landry et al., "Galloxane and Alumoxane Hydroxides: [Ga$_{12}$τBu$_{12}$($\mu_3$–O)$_8$($\mu$–O)$_2$($\mu$–OH)$_4$] and [Al$_6$τBu$_6$($\mu$–O)$_4$($\mu_3$–OH)$_4$]"Angew. Chem. Int. Ed. Engl., 1996, vol. 34, No. 11, pp. 1201–1202.

Mason, et al., "Hydrolysis of Tri–tert–butylaluminum: The First Structural Characterization of Alkylalumoxanes [(R$_2$Al)$_2$O]$_n$ and (RalO)$_n$", J.Am. Chem. Soc., 1993, vol. 115, pp. 4971–4984.

Pieters, et al., "A Method for the Prediction of Metallocene–Type Catalyst Activity in Olefin (co)polymerisation reactions", Macromol Rapid Commun., vol. 16, 1995, pp. 463–467.

Samuel, E. et al., "π–Cyclopentadienyl and π–Indenyl Compounds of Titanium, Zirconium, and Hafnium Containing o–Bonded Organic Substituents[1]", J. Of the Am. Chem. Soc., 1973, vol. 95, pp. 6263–6267.

Small, Brooke L. et al., "Highly Active Iron and Cobalt Catalysts for the Polymerization of Ethylene", J. Am. Chem. Soc., 1998, vol. 120, pp. 4049–4050.

Spaleck, Walter et al., "High Molecular Weight Polypropylene through Specifically Designed Zirconocene Catalysts", Angew. Chem. Int. ED. Engl. 1992, vol. 31, No. 10, pp. 1347–1350.

Storre, Jens et al., "Hydrolysis of Trimesitylgallium and Trimesitylaluminum: Structures Along a Reaction Pathway", J. Am. Chem. Soc., 1996, vol. 118 pp. 1380–1386.

Storre, Jens et al., "A Novel Approach For the Stabilization & Structural Characterization of Group 13 Organometallic Hydroxides: The Way to Well Defined Crystalline Methylalumoxanes", J. Am. Chem. Soc., vol. 119, No. 32, 1997, pp. 7505–7513.

Siedle, A.R. et al., "How Coordinating Are Non–Coordinating Anions?", Macromol. Symp. vol. 89, 1995, pp. 299–305.

Veith, Michael et al., "An Al$_4$(OH)$_4$ Eight–Membered Ring in a Molecular Aluminopolysiloxane and Its Behavior with Bases", Agnew, Chem. Int. Ed. Engl., 1997, vol. 36, No. ½, pp. 117–119.

Chen, You–Xian et al., "Very Large Counteranion Modulation of Cationic Metallocene Polymerization Activity and Stereoregulation by a Sterically Congested (Perfluoroaryl)fluoroaluminate", J. Am. Chem. Soc., vol. 119, No. 10, 1997, pp. 2582–2583.

Brintzinger, Hans H. et al, "Stereospecific Olefin Polymerization with Chiral Metallocene Catalysts", Angew. Chem. Int. Ed Engl., 1995, vol. 34, pp. 1143–1170.

Kaminsky, Walter, "New Polymers by Metallocene Catalysis", Macromolecular Chemistry Phys., 1996, vol. 197, pp. 3907–3945.

Terumasa Yamasaki, "Structure and Lewis acid sites in alumoxane compounds", Catalysis Today, vol. 23, 1995, pp. 425–429.

Hlatky, Gregory G. et al., "Ionic, Base–Free Zirconocene Catalysts for Ethylene Polymerization", J. Am. Chem. Soc. 1989, vol. 111, pp. 2728–2729.

Hlatky, Gregory G. et al., "Supported Ionic Metallocene Polymerization Catalysts", Macromolecules, 1996, vol. pp. 8019–8020.

Ikonitski, I.V. et al., "IR Spectroscopic Study of the Formation of a Complex Alkyalumoxane Catalyst for The Polymerization of α–Oxides of Olefins", pp. 351–354, Translated from Zhurnal Prikladnoi Khimii, vol. 62, No. 394–397, Feb., 1989.

Pasynkiewicz, et al., "Proton Magnetic Resonance Evidence For The Dimethylaluminium Hydroxide", Journal of Organometallic Chemistry, 1977, vol. 124, pp. 265–269.

Manyik, et al., "A Soluble Chromium–based Catalyst For Ethylene Trimerization and Polymerization", Journal of Catalysis, vol. 47, 1977, pp. 197–209.

GELATINOUS COMPOSITIONS FORMED FROM HYDROXYALUMINOXANE, SOLID COMPOSITIONS FORMED THEREFROM, AND THE USE OF SUCH COMPOSITIONS AS CATALYST COMPONENTS

REFERENCE TO RELATED APPLICATIONS

This is a division of prior commonly-owned application Ser. No. 09/946,976, filed Sep. 5, 2001, now U.S. Pat. No. 6,492,292 which is a continuation-in-part of prior U.S. patent application Ser. No. 09/655,218, filed Sep. 5, 2000, now U.S. Pat. No. 6,462,212 and incorporated herein by reference, which is a continuation-in-part of U.S. patent application Ser. No. 09/177,736, filed on Oct. 23, 1998, now U.S. Pat. No. 6,160,145, incorporated herein by reference. This application may also be considered related to U.S. patent application Ser. No. 09/946,881 filed Sep. 5, 2001.

TECHNICAL FIELD

This invention relates to novel compositions of matter which are highly effective as catalyst components, and to the preparation and use of such compositions.

BACKGROUND

Partially hydrolyzed aluminum alkyl compounds known as aluminoxanes (a.k.a. alumoxanes) are effective in activating metallocenes for polymerization of olefins. Activating effects of water in such systems were initially noted by Reichert, et al. (1973) and Breslow, et al. (1975), and extended to trimethylaluminum-based systems by Sinn, Kaminsky, et al. (1976). Subsequent research by Sinn and Kaminsky demonstrated that this activation was due to formation of methylaluminoxane from partial hydrolysis of trimethylaluminum present in the system. Methylaluminoxane (a.k.a. methylalumoxane) has become the aluminum co-catalyst of choice in the industry.

Subsequent to the above original discoveries in this field, considerable worldwide effort has been devoted to improving the effectiveness of catalyst systems based on use of aluminoxanes or modified aluminoxanes for polymerization of olefins and related unsaturated monomers.

Representative of many patents in the field of aluminoxane usage in forming olefin polymerization catalyst systems with suitable metal compounds is U.S. Pat. No. 5,324,800 to Welborn et al. which claims an original filing date in 1983. This patent describes olefin polymerization catalysts made from metallocenes of a metal of Groups 4b, 5b, or 6b, and a cyclic or linear $C_1$–$C_5$ alkylaluminoxane. The cyclic and the linear aluminoxanes are depicted, respectively, by the formulas $(R—Al—O)_n$ and $R(R—Al—O)_n AlR_2$ where n is from 1 to about 20, and R is most preferably methyl. The aluminoxanes are made by controlled hydrolysis of the corresponding aluminum trialkyl.

Another relatively early patent in the field, U.S. Pat. No. 4,752,597 to Turner based on a filing date of 1985, describes olefin polymerization catalysts comprising the reaction products of a metallocene complex of group IVB, VB, VIB, and VIII of the periodic table and an excess of aluminoxane. These catalysts are formed by pre-reacting a metallocene and an aluminoxane in mole ratios greater than 12:1, such as about 12:1 to about 100:1, to produce a solid product which precipitates from solution. Despite assertions of suitable catalytic activity, in reality the activity of these materials is so low as to be of no practical importance whatsoever.

In U.S. Pat. Nos. 4,960,878 and 5,041,584 to Crapo et al. modified methyl-aluminoxane is formed in several ways. One involves reacting a tetraalkyldialuminoxane, $R_2Al—O—AlR_2$, containing $C_2$ or higher alkyl groups with trimethylaluminum (TMA) at –10 to 150° C. Another involves reacting TMA with a polyalkylaluminoxane $(—Al(R)—O—)_n$ where R is $C_2$ alkyl or higher and n is greater than 1, e.g., up to 50. Temperatures suggested for this reaction are –20 to 50° C. A third way involves conducting the latter reaction and then reacting the resultant product, which is indicated to be a complex between trimethylaluminum and the polyalkylaluminoxane, with water. The patent states that the water-to-aluminum ratios used to make the polyalkylaluminoxane reagent have an effect on the activity of the final methylaluminoxane. On the basis of ethylene polymerizations using zirconocene dichloride catalyst and a complex of trimethylaluminum with polyisobutylaluminoxane subsequently reacted with water (MMAO) as co-catalyst, it is indicated in the patent that the highest polymerization activities were achieved with MMAO co-catalyst prepared at $H_2O/Al$ ratios of about 0.6 to about 1.0 and Al/Zr ratios in the range of 10,000/1 to 400,000/1.

Various references are available indicating that isobutylaluminoxanes themselves are relatively ineffective on their own as co-catalysts. For example, several other reactions of alkylaluminum compounds with water are disclosed in U.S. Pat. Nos. 4,960,878 and 5,041,584. Thus in Example 1 of these patents, DIBAL-O (tetraisobutyldialuminoxane), a commercial product, was prepared by reaction of water with triisobutylaluminum (TIBA) in heptane using a water/TIBA ratio of about 0.5, followed by solvent stripping at 58–65° C. under vacuum. In Examples 3–6 of the patents isobutylaluminoxane (IBAO) was prepared by controlled addition of water to a 25% solution of TIBA in toluene in the temperature range of 0–12° C., followed by heating to 70–80° C. to ensure complete reaction and remove dissolved isobutane. $H_2O/Al$ ratios used were 0.98, 1.21, 1.14, and 0.88. IBAO was again made in a similar manner in Example 52 of the patents. Here the $H_2O/Al$ ratio was 0.70, and the product was heated at 75° C. And in Example 70 tri-n-butylaluminum (TNBA) in toluene was treated at 0–10° C. with water followed by heating to 85° C. Ethylene polymerizations using zirconocene dichloride catalyst and various products from the foregoing Examples were conducted. Specific activities ($\times 10^3$; gPE/(gZr·atm $C_2H_4$·hr)) of the catalysts made with DIBAL-O from Ex. 1, IBAO from Ex. 3, and IBAO from Ex. 6 were, respectively, 4.1, 4.2, and 7.7, as compared to 1000 for the catalyst made using conventional MAO as the co-catalyst. The patents acknowledge that tetraisobutyldialuminoxane (DIBAL-O) showed "poor polymerization activity", and from the foregoing test results the same can be said to apply to IBAO.

WO 96/02580 to Dall'occo, et al. describes olefin polymerization catalysts made by contacting a metallocene of Ti, Zr, or Hf, an organoaluminum compound having at least one specified hydrocarbon substituent on the β-carbon atom of an aliphatic group bonded to an aluminum atom, and water. Various ways of bringing these components together are suggested. Polymerizations described were carried out using Al/Zr mole ratios ranging from 500 up to as high as 5000.

EP 0 277 004 to Turner, published in 1988, describes the successful preparation and use as catalysts composed of an ionic pair derived from certain metallocenes of Group 4, most preferably bis(cyclopentadienyl)zirconium dimethyl or bis(cyclopentadienyl)hafnium dimethyl, reacted with certain trisubstituted ammonium salts of a substituted or unsubstituted aromatic boron compound, most preferably N,N-dimethylanilinium tetra(pentafluorophenyl) boron. While EP 0 277 004 mentions that compounds containing an element of Groups V-B, VI-B, VII-B, VIII, I-B, II-B, III-A, IV-A, and V-A may be used in forming the catalysts, no specific compounds other than boron compounds are identified. In fact, EP 0 277 004 appears to acknowledge inability to identify specific compounds other than boron compounds by stating: "Similar lists of suitable compounds containing other metals and metalloids which are useful as second components could be made, but such lists are not deemed necessary to a complete disclosure." See in this connection Hlatky, Turner and Eckman, *J. Am. Chem. Soc.*, 1989, 111, 2728–2729, and Hlatky and Upton, *Macromolecules*, 1996, 29, 8019–8020.

U.S. Pat. No. 5,153,157 to Hlatky and Turner states that its process "is practiced with that class of ionic catalysts referred to, disclosed, and described in European Patent Applications 277,003 and 277,004." The process of U.S. Pat. No. 5,153,157 involves forming an ionic catalyst system from two components. The first is a bis(cyclopentadienyl) derivative of a Group IV-B metal compound containing at least one ligand which will combine with the second component or portion thereof such as a cation portion thereof. The second component is referred to as an ion exchange compound comprising (1) a cation which will irreversibly react with a ligand of the Group IV-B metal compound and (2) a noncoordinating anion which is bulky, labile, and stable. The second component, also termed an activator component, comprises compounds of Groups V-B, VI-B, VII-B, VIII, I-B, II-B, III-A, IV-A, and V-A identified by a general formula. Besides referring to the boron compounds of EP 277,004, supra, such as tri(n-butylammonium)tetra (pentafluorophenyl)boron and N,N-dimethyl-anilinium tetra (pentafluorophenyl)boron as suitable activators, the U.S. '157 patent teaches use of boron compounds having a plurality of boron atoms, and also trialkyl aluminum compounds, triaryl aluminum compounds, dialkylaluminum alkoxides, diarylaluminum alkoxides, and analogous compounds of boron. Of the organoaluminum activators triethylaluminum and trimethylaluminum are specified as most preferred. The Examples show use of a catalyst system formed from (1) a solution of bis(cyclopentadienyl) zirconium dimethyl or bis(cyclopentadienyl)hafnium dimethyl and N,N-dimethylanilinium tetra(pentafluorophenyl) boron together with (2) triethylborane, triethylaluminum, tri-sec-butylborane, trimethylaluminum, and diethylaluminum ethoxide. In some cases the catalyst formed from the metallocene and the N,N-dimethylanilinium tetra (pentafluorophenyl)boron without use of a compound of (2) gave no polymer at all under the polymerization conditions used.

U.S. Pat. No. 5,198,401 to Turner, Hlatky, and Eckmnan refers, in part, to forming catalyst compositions derived from certain metallocenes of Group 4, such as bis (cyclopentadienyl)zirconium dimethyl or bis (cyclopentadienyl)hafnium dimethyl, reacted with certain trisubstituted ammonium salts of a substituted or unsubstituted aromatic boron compound, such as N,N-dimethylanilinium tetra(pentafluorophenyl)boron or tributylammonium tetra(pentafluorophenyl)boron as in EP 0 277 004. However here the anion is described as being any stable and bulky anionic complex having the following molecular attributes: 1) the anion should have a molecular diameter about or greater than 4 angstroms; 2) the anion should form stable salts with reducible Lewis acids and protonated Lewis bases; 3) the negative charge on the anion should be delocalized over the framework of the anion or be localized within the core of the anion; 4) the anion should be a relatively poor nucleophile; and 5) the anion should not be a powerful reducing or oxidizing agent. Anions of this type are identified as polynuclear boranes, carboranes, metallacarboranes, polyoxoanions and anionic coordination complexes. Elsewhere in the patent it is indicated that any metal or metalloid capable of forming a coordination complex which is resistant to degradation by water (or other Brønsted or Lewis acids) may be used or contained in the second activator compound [the first activator compound appears not to be disclosed]. Suitable metals of the second activator compound are stated to include, but not be limited to, aluminum, gold, platinum and the like. No such compound is identified. Again after listing boron compounds the statement is made that "Similar lists of suitable compounds containing other metals and metalloids which are useful as second components could be made, but such lists are not deemed necessary to a complete disclosure." In this connection, again note Hlatky, Turner and Eckman, *J. Am. Chem. Soc.*, 1989, 111, 2728–2729, and Hlatky and Upton, *Macromolecules*, 1996, 29, 8019–8020.

Despite the above and many other efforts involving aluminum co-catalysts, the fact remains that in order to achieve suitable catalysis on a commercial basis, relatively high aluminum to transition metal ratios must be employed. Typically for optimal activity an aluminum to metallocene ratio of greater than about 1000:1 is required for effective homogeneous olefin polymerization. According to Brintzinger, et al., *Angew. Chem. Int. Ed. Engl.*, 1995, 34 1143–1170:

"Catalytic activities are found to decline dramatically for MAO concentrations below Al:Zr ratio roughly 200–300:1. Even at Al:Zr ratios greater than 1000:1 steady state activities increase with rising MAO concentrations approximately as the cube root of the MAO concentration".

This requirement of high aluminum loading is mainly caused by a metallocene activation mechanism in which generation of catalytically active species is equilibrium driven. In this role MAO acts as a Lewis acid to remove by group transfer a leaving group $X^{\ominus}$ from the transition metal. This forms a weakly-coordinating anion, MAO-$X^{\ominus}$, in the corresponding transition metal cation. That is, in such systems the following equilibrium exists:

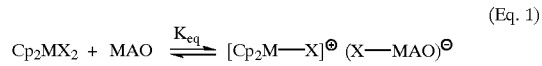

(Eq. 1)

The Lewis acid sites in MAO abstract a negatively charged leaving group such as a methide group from the metallocene to form the catalytically active ion pair. The activation process is reversible and $K_{eq}$ is typically small. Thus the ion pair can return to its neutral precursors which are catalytically inactive. To overcome this effect, a large excess of MAO is required to drive the equilibrium to the right.

The high aluminum loadings required for effective catalysis in such systems result in the presence of significant levels of aluminum-containing residues ("ash") in the polymer. This can impair the clarity of finished polymers formed from such catalyst systems.

A further disadvantage of MAO is its limited solubility in paraffinic hydrocarbon solvents. Polymer manufacturers would find it of considerable advantage to have in hand aluminoxane and metallocene-based materials having high paraffin solubility.

Still another disadvantage of MAO has been its relatively high cost. For example, in an article entitled "Economics is Key to Adoption of Metallocene Catalysts" in the Sept. 11, 1995 issue of Chemical & Engineering News, Brockmeier of Argonne National Laboratory concluded that "a reduction in costs or amount of MAO has the potential for greatly reducing the costs to employ metallocene catalysts".

Thus it would be of inestimable value to the art if a way could be found of providing catalyst components based on use of aluminoxanes that are effective co-catalysts for use with transition metal compounds at much lower aluminum-:metal ratios than have been effective heretofore. In addition, the art would be greatly advanced if this could be accomplished with aluminoxane compositions that are less expensive than MAO, that have high solubility in paraffinic solvents and that produce lower ash residues in the polymers.

The invention described and claimed in U.S. Pat. No. 6,160,145 is deemed to have fulfilled most, if not all, of the foregoing desirable objectives. In brief summary, that invention makes it possible to provide catalyst compositions in which a low cost co-catalyst can be employed at very low Al loadings. Such catalyst compositions typically have high solubility in paraffinic solvents. Moreover they yield reduced levels of ash and result in improved clarity in polymers formed from such catalyst compositions. Making all of this possible is the provision of a compound which comprises (i) a cation derived from a transition, lanthanide or actinide metal compound, preferably a metallocene, by loss of a leaving group, and (ii) an aluminoxate anion (a.k.a. aluminoxanate anion) derived by transfer of a proton from a stable or metastable hydroxyaluminoxane to said leaving group. In contrast to aluminoxanes used prior to the Parent Application and acting as Lewis acids (Eq. 1), the present compositions utilize hydroxyaluminoxane species (HO-AO) acting as Brønsted acids. In the formation of such compounds, a cation is derived from the transition, lanthanide or actinide metal compound by loss of a leaving group, and this cation forms an ion pair with an aluminoxate anion devoid of such leaving group. The leaving group is typically transformed into a neutral hydrocarbon thus rendering the catalyst-forming reaction irreversible as shown in Equation 2:

(Eq. 2)

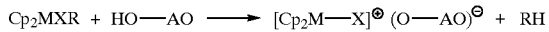

$Cp_2MXR + HO{-}AO \longrightarrow [Cp_2M{-}X]^{\oplus} (O{-}AO)^{\ominus} + RH$ Note the absence of the leaving group, X, in the anion $OAO^{\ominus}$ as compared to the presence of X in the anion, $(X{-}MAO)^{\ominus}$, of Equation 1.

In many of the patents related to the use of aluminoxanes as metallocene co-catalysts, rather broad and generalized assertions have been routinely made regarding aluminum-to-metallocene ratio, types of alkyl aluminoxanes, and ratio of water to aluminum for forming aluminoxanes. However, there is no disclosure of any type that would suggest, let alone demonstrate, the use of an aluminoxane as a Brønsted acid to activate metallocenes and related organometallic catalysts. There are, furthermore, no known prior teachings or descriptions of how to use an aluminoxane as a Brønsted acid muchless that by so doing it would be possible to reduce the ratio of aluminum to transition, lanthanide or actinide metal to an unprecedentedly low level.

In another of its embodiments the invention of U.S. Pat. No. 6,160,145 provides a process which comprises contacting a transition, lanthanide or actinide metal compound having at least two leaving groups with a hydroxyaluminoxane in which at least one aluminum atom has a hydroxyl group bonded thereto so that one of said leaving groups is lost. As noted above, during the formation of such compounds, an aluminoxate anion is formed that is devoid of the leaving group. Instead the leaving group is typically transformed into a neutral hydrocarbon so that the catalyst forming reaction is irreversible.

Still another embodiment of the invention of U.S. Pat. No. 6,160,145 is a process of polymerizing at least one polymerizable unsaturated monomer, which process comprises contacting said monomer under polymerization conditions with a compound which comprises a cation derived from a transition, lanthanide or actinide metal compound, preferably a metallocene, by loss of a leaving group and an aluminoxate anion derived by transfer of a proton from a stable or metastable hydroxyaluminoxane to said leaving group.

Other embodiments of the invention of U.S. Pat. No. 6,160,145 include catalyst compositions in which a compound comprising a cation derived from a transition, lanthanide or actinide metal compound, preferably a metallocene, by loss of a leaving group and an aluminoxate anion derived by transfer of a proton from a stable or metastable hydroxyaluminoxane to said leaving group is supported on a carrier.

As described in U.S. patent application Ser. No. 09/655, 218, filed Sep. 5, 2000, now U.S. Pat. No. 6,492,292 (hereinafter the "'218 Application"), the catalyst compositions as described in U.S. Pat. No. 6,160,145 and also herein can have exceptional stability once recovered and maintained under suitable conditions in the absence of a solvent. The '218 Application describes storage of a solid catalyst of this type in a drybox at ambient room temperatures for a one-month period without loss of its catalytic activity. In contrast, the same catalyst composition is relatively unstable if left in the reaction solution or put in solution after it has been removed from solution. The added features of this invention are to recover the catalyst composition (catalytic compound) after its preparation, optionally subject the catalyst composition to one or more finishing procedures and/or optionally mix the catalyst composition with one or more inert substances under suitable inert anhydrous conditions, and store the catalyst composition by itself, in supported form or as a solvent-free mixture with one or more inert substances under suitable conditions which minimize exposure to moisture and air (oxygen) as much as reasonably possible.

Thus in one of the embodiments described in the '218 Application is a compound which comprises a cation derived from d-block or f-block metal compound by loss of a leaving group and an aluminoxate anion derived by transfer of a proton from a stable or metastable hydroxyaluminoxane to said leaving group, wherein such compound is in undissolved form in a dry, inert atmosphere or environment. Preferably the compound in such atmosphere or environment is in isolated form or is in supported form on a catalyst support.

Another embodiment described in the '218 Application is a compound which comprises a cation derived from a d-block or f-block metal compound by loss of a leaving group and an aluminoxate anion devoid of said leaving group, wherein the compound comprised of such cation and aluminoxate anion is in undissolved form in a dry, inert atmosphere or environment. Preferably the compound in such atmosphere or environment is in isolated form or is in supported form on a catalyst support.

A further embodiment described in the '218 Application is a compound which comprises a cation derived from a d-block or f-block metal compound by loss of a leaving group transformed into a neutral hydrocarbon, and an aluminoxate anion derived by loss of a proton from a hydroxyaluminoxane having, prior to said loss, at least one aluminum atom having a hydroxyl group bonded thereto, wherein the compound comprised of such cation and aluminoxate anion is in undissolved form except during one or more optional finishing procedures, if and when any such finishing procedure is performed. In addition, the compound is kept in a dry, inert atmosphere during a storage period. Preferably the compound in such atmosphere or environment is in isolated form or is in supported form on a catalyst support.

The compounds of each of the above embodiments of the '218 Application can be used as a catalyst either in the solid state or in solution. The stability of the compound when in solution is sufficient to enable the compound to perform as a homogeneous catalyst.

Still another embodiment described in the '218 Application is a process which comprises contacting a d-block or f-block metal compound having at least two leaving groups with a hydroxyaluminoxane in which at least one aluminum atom has a hydroxyl group bonded thereto so that one of said leaving groups is lost; recovering the resultant metal-containing compound so formed; and storing such recovered compound (preferably in isolated form or in supported form on a catalyst support) in an anhydrous, inert atmosphere or environment. Such compound is maintained in undissolved form except during one or more optional finishing procedures, if and when any such finishing procedure is performed.

Also provided as another embodiment of the '218 Application is a process which comprises donating a proton from an aluminoxane to a leaving group of a d-block or f-block metal compound to form a compound composed of a cation derived from said metal compound and an aluminoxate anion devoid of said leaving group; recovering the compound composed of such cation and aluminoxate anion; storing such recovered compound (preferably in isolated form or in supported form on a catalyst support) in an anhydrous, inert atmosphere or environment; and maintaining such compound in undissolved form except during one or more optional finishing procedures, if and when any such finishing procedure is performed.

Another embodiment of the '218 Application is a process which comprises interacting a d-block or f-block metal compound having two leaving groups and a hydroxyaluminoxane having at least one aluminum atom that has a hydroxyl group bonded thereto to form a compound composed of a cation through loss of a leaving group which is transformed into a neutral hydrocarbon, and an aluminoxate anion derived by loss of a proton from said hydroxyaluminoxane; recovering the compound composed of such cation and aluminoxate anion; storing such recovered compound (preferably in isolated form or in supported form on a catalyst support) in an anhydrous, inert atmosphere or environment; and maintaining such compound in undissolved form except during one or more optional finishing procedures, if and when any such finishing procedure is performed.

Still other embodiments are described in the '218 Application.

Notwithstanding all of the foregoing advances, the metastable nature of the hydroxy groups in the hydroxyaluminoxane species of aluminoxanes can have an negative impact upon the shelf life of this species of compounds. Increasing the steric bulk of these compounds does appear to increase the lifetime of their OH groups (see, e.g., FIG. 6), but not sufficiently to meet the anticipated needs of commercial applications. Storage of these compounds at low temperature, e.g., circa −10° C., can significantly increase the compound lifetime (see, e.g., FIG. 7), but cost and operational considerations of this technique also are less that ideal for commercial applications.

Accordingly, a need exists for a way to significantly increasing the lifetime of the OH groups in hydroxyaluminoxanes, preferably at or near room temperature. A need also exists for a facile way to employ olefin polymerization catalysts while avoiding reactor fouling.

BRIEF SUMMARY OF THE INVENTION

The present invention is deemed to meet these and other needs in a surprisingly novel way. It has now been found that hydroxyaluminoxanes can be converted into novel compositions of matter in gelatinous form, or in solid form formed from the gelatinous form, or in both forms, so as to drastically increase the lifetime of the hydroxy group(s) in the composition (i.e., reduce the composition OH-decay rate), even at room temperature, while at the same time reducing, if not eliminating, reactor fouling. When the term "gelatinous" is used herein, it denotes that the composition is in a jelly-like form which either may be composed of a gelled solution or suspension formed from the hydroxyaluminoxane and of sufficiently viscous consistency to act like a gel or jelly.

Thus, this invention provides in one of its embodiments a composition of matter in gelatinous form, or in solid form derived therefrom, or both, formed by bringing together at least (i) a hydroxyaluminoxane in an inert solvent and (ii) a treating agent, such that the composition has a reduced OH-decay rate as compared to the OH-decay rate of the hydroxyaluminoxane. Without being bound to theory, it is believed that the gelatinous continuous phase is a matrix formed from the hydroxyaluminoxane upon being exposed to sufficient amounts of the treating agent. Another embodiment of the invention is a solid composition of matter formed by removing said inert solvent from the composition of matter in gelatinous form.

In another embodiment, a gelatinous composition is comprised of hydroxy-aluminoxane and characterized by having an OH-decay rate which is reduced as compared to the OH-decay rate of the hydroxyaluminoxane in a liquid form.

Another embodiment of this invention provides a process comprising converting a hydroxyaluminoxane into a gelatinous composition of matter by bringing together (i) said hydroxyaluminoxane in an inert solvent and (ii) a treating agent compatible with said hydroxyaluminoxane, whereby the rate of OH-decay for said composition of matter is reduced relative to the rate of OH-decay of (i).

Still another embodiment of the invention yields an activated catalyst composition formed by bringing together (A) a gelatinous composition of matter, or a solid composition of matter formed therefrom, or both, said gelatinous composition of matter being formed by bringing together at least (i) a hydroxyaluminoxane in an inert solvent and (ii) a treating agent compatible with said hydroxyaluminoxane, said gelatinous composition of (A) having a reduced OH-decay rate relative to the OH-decay rate of (i); and (B) a d- or f-block metal compound having at least one leaving group on a metal atom thereof.

This invention also provides an embodiment which is a process of preparing an activated olefin polymerization catalyst composition, which process comprises bringing together (A) a gelatinous composition of matter, or a solid composition of matter formed therefrom, or both, said gelatinous composition of matter being formed by bringing together at least (i) a hydroxyaluminoxane in an inert solvent and (ii) a treating agent compatible with said hydroxyaluminoxane, whereby the rate of OH-decay for said composition is reduced relative to the rate of OH-decay of (i); and (B) a d- or f-block metal compound having at least one leaving group on a metal atom thereof.

A further embodiment of the invention is an olefin polymerization process which comprises bringing together in a polymerization reactor or reaction zone at least (1) one or more polymerizable olefins and (2) an activated catalyst composition which is in accordance with the present invention, so as to form a polymer.

Yet another embodiment of the invention is a process which comprises bringing together at least (i) an aluminum alkyl in an inert solvent and (ii) a water source, under hydroxyaluminoxane-forming reaction conditions and using an amount of (ii) sufficient to cause a gelatinous composition of matter to form.

The above and other embodiments, features, and advantages of this invention will become still further apparent from the ensuing description and appended claims.

FURTHER DETAILED DESCRIPTION OF THE INVENTION

Hydroxyaluminoxane Reactants

Figure 1:
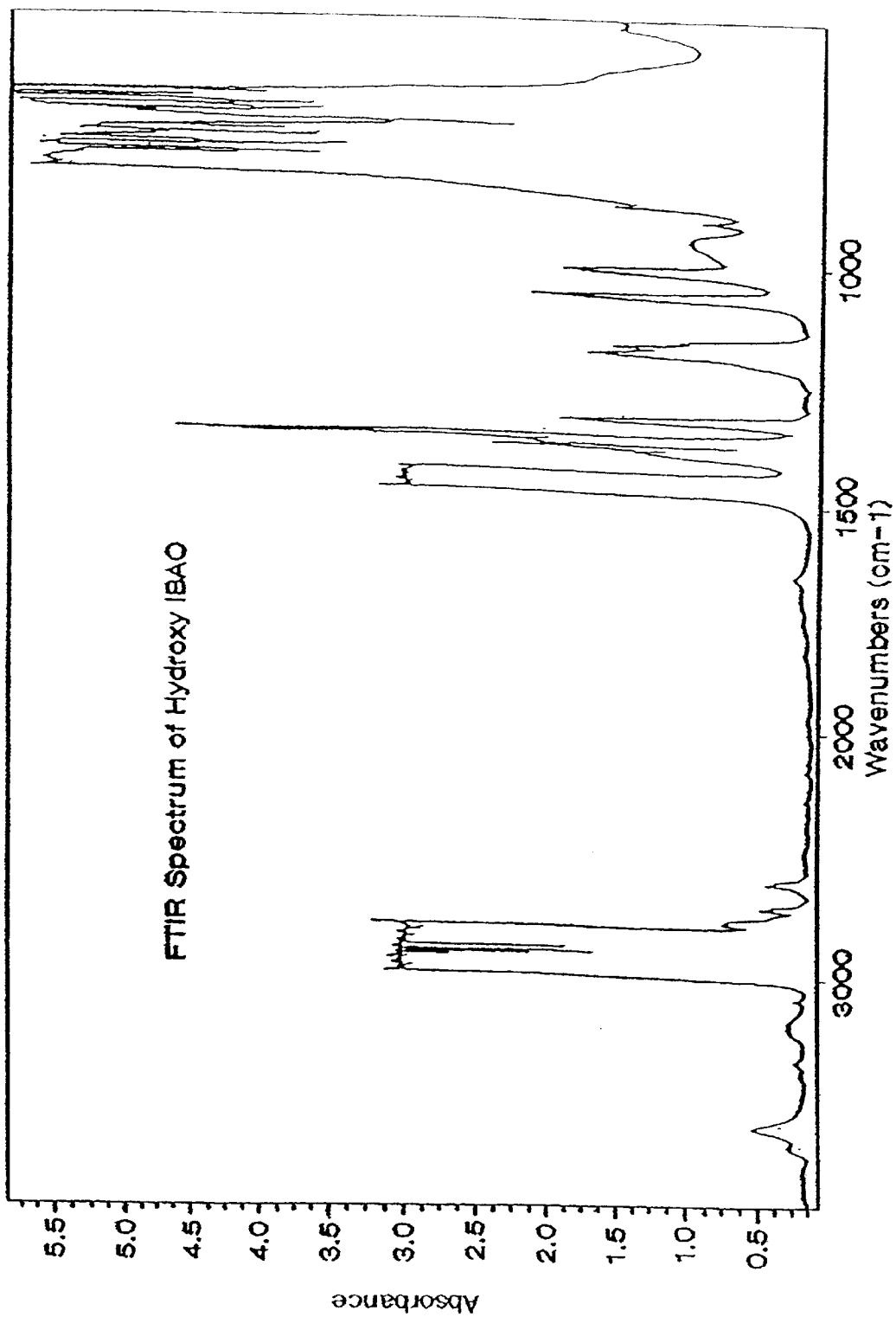
FIG. 1 is an infrared spectrum of hydroxyisobutylaluminoxane (HO-IBAO) useful in the practice of this invention.

Unlike catalyst compositions formed from a transition, lanthanide or actinide metal compound (hereinafter "d- or f-block metal compound") and MAO or other previously recognized aluminoxane co-catalyst species, the catalyst compositions of U.S. Pat. No. 6,160,145 and U.S. patent application Ser. No. 09/655,218 are formed from a hydroxyaluminoxane. The hydroxyaluminoxane has a hydroxyl group bonded to at least one of its aluminum atoms. To form these hydroxyaluminoxanes, a sufficient amount of water is reacted with an alkyl aluminum compound to result in formation of a compound having at least one HO—Al group and having sufficient stability to allow reaction with a d- or f-block organometallic compound to form a hydrocarbon.

The alkyl aluminum compound used in forming the hydroxyaluminoxane reactant can be any suitable alkyl aluminum compound other than trimethylaluminum. Thus at least one alkyl group has two or more carbon atoms. Preferably each alkyl group in the alkyl aluminum compound has at least two carbon atoms. More preferably each alkyl group has in the range of 2 to about 24, and still more preferably in the range of 2 to about 16 carbon atoms. Particularly preferred are alkyl groups that have in the range of 2 to about 9 carbon atoms each. The alkyl groups can be cyclic (e.g., cycloalkyl, alkyl-substituted cycloalkyl, or cycloalkyl-substituted alkyl groups) or acyclic, linear or branched chain alkyl groups. Preferably the alkyl aluminum compound contains at least one, desirably at least two, and most preferably three branched chained alkyl groups in the molecule. Most preferably each alkyl group of the aluminum alkyl is a primary alkyl group, i.e., the alpha-carbon atom of each alkyl group carries two hydrogen atoms.

Suitable aluminum alkyl compounds which may be used to form the hydroxyaluminoxane reactant include dialkylaluminum hydrides and aluminum trialkyls. Examples of the dialkylaluminum hydrides include diethylaluminum hydride, dipropylaluminum hydride, diisobutylaluminum hydride, di(2,4,4-trimethylpentyl)aluminum hydride, di(2-ethylhexyl)aluminum hydride, di(2-butyloctyl)aluminum hydride, di(2,4,4,6,6-pentamethylheptyl)aluminum hydride, di(2-hexyldecyl)aluminum hydride, dicyclopropylcarbinylaluminum hydride, dicyclohexylaluminum hydride, dicyclopentylcarbinylaluminum hydride, and analogous dialkylaluminum hydrides. Examples of trialkylaluminum compounds which may be used to form the hydroxyaluminoxane include triethylaluminum, tripropylaluminum, tributylaluminum, tripentylaluminum, trihexylaluminum, triheptylaluminum, trioctylaluminum, and their higher straight chain homologs; triisobutylaluminum, tris(2,4,4-trimethylpentyl)aluminum, tri-2-ethylhexylaluminum, tris(2,4,4,6,6-pentamethylheptyl)aluminum, tris(2-butyloctyl)aluminum, tris(2-hexyldecyl)aluminum, tris(2-heptylundecyl)aluminum, and their higher branched chain homologs; tri(cyclohexyl-carbinyl)aluminum, tri(2-cyclohexylethyl)aluminum and analogous cycloaliphatic aluminum trialkyls. Triisobutylaluminum has proven to be an especially desirable alkyl aluminum compound for producing a hydroxyaluminoxane.

To prepare the hydroxyaluminoxane a solution of the alkyl aluminum compound in an inert solvent, preferably a saturated or aromatic hydrocarbon, is treated with controlled amounts of water while maintaining the vigorously agitated reaction mixture at low temperature, e.g., below about 0° C. When the exothermic reaction subsides, the reaction mixture is stored at a low temperature, e.g., below about 0° C. until used in forming a compound of this invention. When preparing a hydroxyaluminoxane from a low molecular weight alkylaluminum compound, the reaction mixture can be subjected, if desired, to stripping under vacuum at a temperature below room temperature to remove some lower alkane hydrocarbon co-product formed during the reaction. However, such purification is usually unnecessary as the lower alkane co-product is merely an innocuous impurity.

Among suitable procedures for preparing hydroxyaluminoxanes for use in practice of this invention, is the method described by Ikonitskii et al., *Zhurnal Prikladnoi Khimii*, 1989, 62(2), 394–397; and the English language translation thereof available from Plenum Publishing Corporation, copyright 1989, as Document No. 0021-888X/89/6202-0354.

Figure 2:
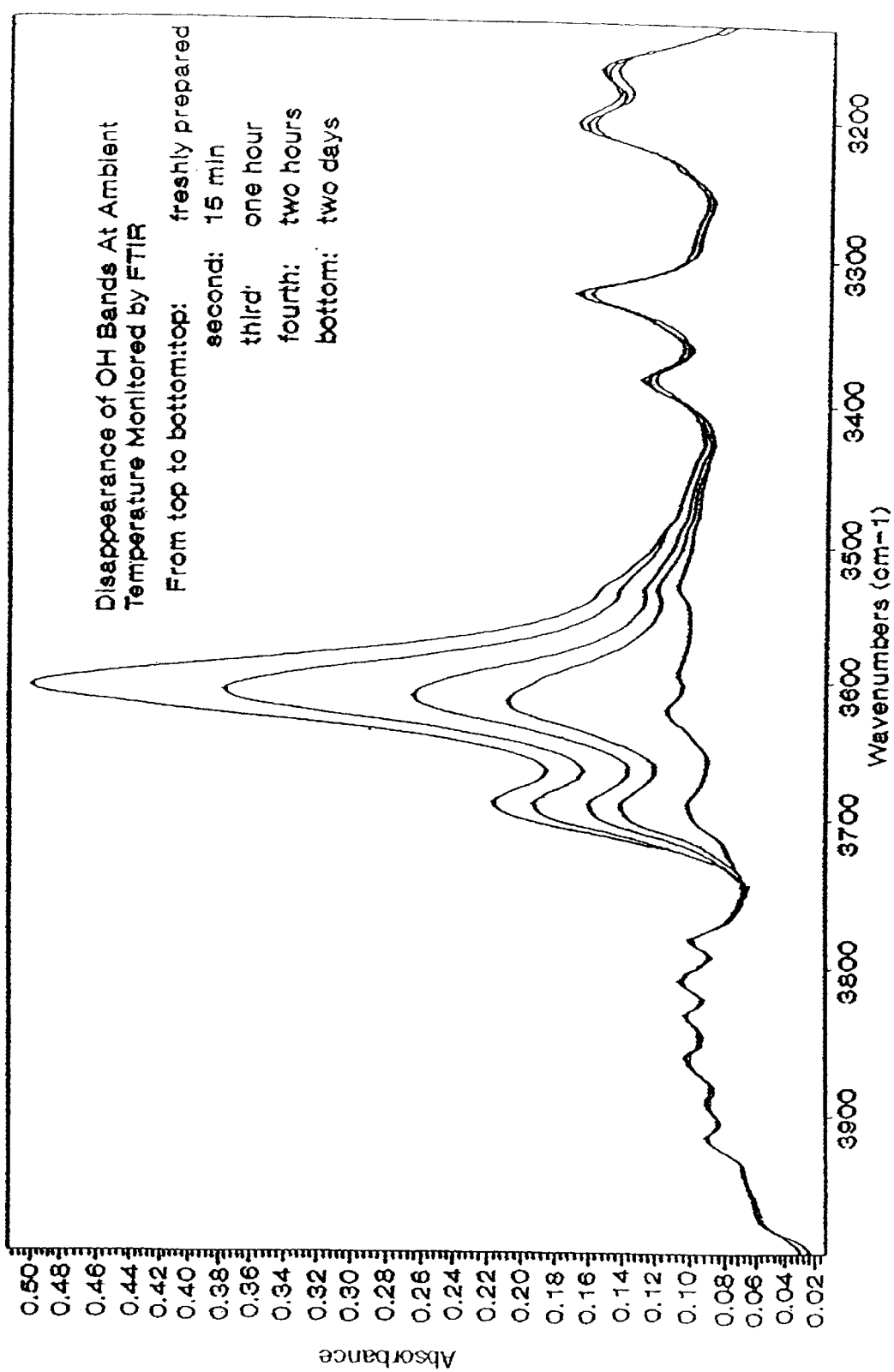
FIG. 2 is a superimposed series of infrared spectra of HO-IBAO illustrating the loss of hydroxyl groups at intervals during a two-day period at ambient temperature.

It is very important to slow down the premature loss of its hydroxyl group content sufficiently to maintain a suitable level of OH groups until the activation reaction has been effected. One way to accomplish this is to maintain the temperature of the hydroxyaluminoxane product solution sufficiently low. This is demonstrated by the data presented graphically in FIG. 2 which shows the loss of hydroxyl groups from hydroxyisobutylaluminoxane at ambient room temperature in an IR cell. If, on the other hand, the same hydroxyaluminoxane solution is stored in a freezer at $-10°$ C., the rate of hydroxyl group loss is reduced to such a degree that the time scale for preserving the same amount of hydroxyl groups can be lengthened from one to two hours at ambient room temperature to one to two weeks at $-10°$ C. If the hydroxyl group content is lost, the compound reverts to an aluminoxane which is incapable of forming the novel ionic highly active catalytic compounds of this invention.

It is also important when preparing the hydroxyaluminoxanes to use enough water to produce the hydroxyaluminoxane, yet not so much water as will cause its destruction. Typically the water/aluminum mole ratio is in the range of about 0.5/1 to about 1.2/1, and preferably in the range of 0.8/1 to 1.1/1. At least in the case of hydroxyisobutylaluminoxane, these ratios typically result in the formation of hydroxyaluminoxane having at least about one hydroxyl group for every seven aluminum atoms in the overall product. The hydroxyisobutylaluminoxane is essentially devoid of unreacted triisobutylaluminum.

However, it now has been discovered that the rate of OH-decay (i.e., the rate at which OH groups disassociate so as to reduce the number of OH groups present in the molecule) of the above-described hydroxyalumioxane may be drastically and surprisingly reduced by converting hydroxyaluminoxane in an inert solvent into a gelatinous composition of matter, or into a solid composition of matter formed from said gelatinous composition of matter, or into a mixture of said solid and said gelatinous composition, whereby the rate of OH-decay for the gelatinous composition, the solid composition, or the mixture is reduced as compared to the rate of OH-decay for the hydroxyaluminoxane. The inert solvent which forms solution with the hydroxyaluminoxane should be inert to the other materials involved and is typically a liquid paraffinic or aromatic hydrocarbon solvent such as, e.g., heptane, isooctane, decane, toluene, xylene, ethylbenzene, mesitylene, or mixtures of liquid paraffinic hydrocarbons and/or liquid aromatic hydrocarbons. The amount of inert solvent present can vary widely, but typically will be at least enough to dissolve the hydroxyaluminoxane. The gelatinous composition is formed by bringing together the hydroxyaluminoxane in an inert solvent and a treating agent which is compatible with the hydroxyaluminoxane. The solid composition may be formed by removal of the inert solvent from the gelatinous composition by, for example, solvent stripping. This solid composition of matter may also serve as a co-catalyst component in forming the olefin polymerization catalyst. Without being bound to theory, both the gelatinous and the solid co-catalyst compositions of matter appear to remain active as a Brønsted acid for a surprisingly greater period of time as compared to that of the hydroxyaluminoxane.

When it is stated herein that the treating agent is considered "compatible" with the hydroxyaluminoxane, it is meant that the treating agent is capable of coming into proximity or contact with, or being mixed with or otherwise placed in the presence of, the hydroxyaluminoxane without adversely affecting the ability of the hydroxyaluminoxane to activate the metal compound elsewhere described herein to form the polymerization catalysts of this invention.

Typically, the rate of OH-decay for the composition so formed is reduced by a factor of at least 5, and more preferably at least 10, as compared to the rate of OH-decay of the hydroxyaluminoxane. The gelatinous composition formed by bringing together at least the hydroxyaluminoxane in an inert solvent and the treating agent may be used to form active polymerization catalysts of this invention.

The treating agent employed to form the co-catalysts of this invention is preferably free water, but may alternatively be a hydrate of alkali or alkaline earth metal hydroxides such as, for example, lithium, sodium, potassium, barium, calcium, magnesium, and cesium hydroxides (e.g., sodium hydroxide mono- and dihydrate, barium hydroxide octahydrate, potassium hydroxide dihydrate, cesium hydroxide monohydrate, lithium hydroxide monohydrate, and the like), aluminum sulfate, as well as mixtures of any two or more of the foregoing.

One preferred method of converting the hydroxyaluminoxane in an inert solvent into a gelatinous composition of matter is mixing the hydroxyaluminoxane in an inert solvent with a gel-forming amount of the treating agent. The amount of treating agent necessary to be gel-forming will vary, depending upon the hydroxyaluminoxane involved. The amount of treating agent employed must at least be sufficient to cause the gelatinous composition to form. When the hydroxyaluminoxane is hydroxyisobutylaluminoxane and the treating agent is free water, for example, the amount of water is preferably sufficient to provide a water to aluminum molar ratio which exceeds about 1.10.

The treating agent may be brought together with the hydroxyaluminoxane in an inert solvent by any number of ways such as mixing, contacting, co-feeding, etc. employing any sequence of addition. Preferably, the treating agent will be added slowly (e.g., dropwise) to the hydroxyaluminoxane and solvent solution. It is also preferable that the treating agent and hydroxyaluminoxane in solvent be brought together at relatively low temperature (i.e., at or below $10°$ C.) and under an inert atmosphere such as, e.g., nitrogen. The reaction conditions are not pressure dependent, as atmospheric, subatmospheric and superatmospheric pressure may be employed, with the pressure conditions preferably being selected to avoid hindering formation of the gelatinous composition.

For quantitative purposes with respect to the number of hydroxyl groups present in the hydroxyaluminoxane or in the composition made therefrom, typically samples will be stored at room temperature in a dry box and sampled periodically for quantitative analysis to determine the rate of OH-decay at given points in time. A typical procedure with respect to hydroxyisobutylaluminoxane gel may employ FT-IR spectra as described below in the paragraph immediately preceding Example 21. This procedure will preferably be employed to quantify the hydroxyl groups (as HO- per 100 aluminum atoms) present in the composition at or near the time of fresh preparation (i.e., time zero), and at one or more intervals of time thereafter, preferably at 48 hours or more preferably at 72 hours following preparation of the sample materials. The change in the number of hydroxyl groups at the selected time interval from that at time zero, divided by the amount of time, will be the OH-decay rate.

These co-catalyst compositions formed from the hydroxyaluminoxane in inert solvent and the treating agent may be formed and isolated (e.g., by solidifying through solvent stripping) prior to use as a catalyst component, or they may be formed in situ, such as, e.g., during the process of production of the hydroxyaluminoxane itself or even production of the desired activated catalyst. Accordingly, these compositions may be formed by addition of sufficient amounts of the treating agent during the synthesis of hydroxyaluminoxane. For example, the water source employed to form the initial hydroxyaluminoxane may also function as the treating agent when a sufficient amount of the water source is added so as to form the gelatinous composition of matter. Besides free water, other non-limiting examples of a suitable water source include the same examples as given for the treating agent. Free water is preferred. The reaction conditions for this in situ formation of the gelatinous composition of matter will typically be the same as those reactions conditions taught herein for forming the hydroxyaluminoxane generally. Once the gelatinous composition is formed, or the solid composition derived from the gelatinous composition, or a mixture of both, is formed, the composition or mixture may be brought together (e.g., by mixing, contacting, co-feeding, etc.) with a d- or f-block metal compound described hereinafter, using reaction conditions as hereinafter described so as to form the activated olefin polymerization catalyst in a single pot process.

When forming the co-catalyst composition from the hydroxyaluminoxane in inert solvent and the treating agent, it is preferred that the hydroxyaluminoxane have less than 25 OH groups per 100 aluminum atoms, and even more preferred that the hydroxyaluminoxane have no more than 15 OH groups per 100 aluminum atoms. In certain other embodiments of this invention, it is also preferred that the composition so made be substantially insoluble in an inert organic solvent such as various liquid hydrocarbons, e.g., liquid saturated aliphatic or cycloaliphatic hydrocarbons. Hydroxyisobutylaluminoxane is particularly preferred as the hydroxyaluminoxane.

These compositions formed from a hydroxyaluminoxane may be employed as the olefin polymerization co-catalyst in place of the less stable hydroxyaluminoxane, to provide a surprisingly more stable yet equally effective co-catalyst and/or catalyst composition which features substantially reduction if not elimination, of reactor fouling.

d- or f-Block Metal Compound

Various d- and f-block metal compounds may be used in forming the catalytically active compounds of this invention. The d-block and f-block metals of this reactant are the transition, lanthanide and actinide metals. See, for example, the Periodic Table appearing on page 225 of Moeller, et al., *Chemistry*, Second Edition, Academic Press, Copyright 1984. As regards the metal constituent, preferred are compounds of Fe, Co, Pd, and V. More preferred are compounds of the metals of Groups 4–6 (Ti, Zr, Hf. V, Nb, Ta, Cr, Mo, and W), and most preferred are the Group 4 metals, especially hafnium, and most especially zirconium.

A vital feature of the d- or f-block metal compound used in forming the ionic compounds of this invention is that it must contain at least one leaving group that forms a separate co-product by interaction with a proton from the hydroxyaluminoxane or that interacts with a proton from the hydroxyaluminoxane so as to be converted from a cyclic divalent group into an open chain univalent group bonded to the metal atom of the metallocene. Thus the activity of the chemical bond between the d- or f-block metal atom and the leaving group must be at least comparable to and preferably greater than the activity of the aluminum-carbon bond of the hydroxyaluminoxane. In addition, the basicity of the leaving group must be such that the acidity of its conjugate acid is comparable to or less than the acidity of the hydroxyaluminoxane. Univalent leaving groups that meet these criteria include hydride, hydrocarbyl and silanylcarbinyl ($R_3SiCH_2$—) groups, such as methyl, ethyl, vinyl, allyl, cyclohexyl, phenyl, benzyl, trimethylsilanylcarbinyl, amido, alkylamido, substituted alkylamido, etc. Of these, the methyl group is the most preferred leaving group. Suitable divalent cyclic groups that can serve as leaving groups by a ring opening mechanism whereby a cyclic group is converted into an open chain group that is still bonded to the metal atom of the metallocene include conjugated diene divalent anionic ligand groups such as a conjugated diene or a hydrocarbyl-, halocarbyl-, or silyl substituted derivative thereof, such conjugated diene anionic ligand groups having from 4 to about 40 nonhydrogen atoms and being coordinated to the metal atom of the metallocene so as to form a metallocyclopentene therewith. Typical conjugated diene ligands of this type are set forth for example in U.S. Pat. No. 5,539,068.

Metallocenes make up a preferred class of d- and f-block metal compounds used in making the ionic compounds of this invention. These compounds are characterized by containing at least one cyclopentadienyl moiety pi-bonded to the metal atom. For use in this invention, the metallocene must also have bonded to the d- or f-block metal atom at least one leaving group capable of forming a stable co-product on interaction with a proton from the hydroxyaluminoxane. A halogen atom (e.g., a chlorine atom) bonded to such metal atom is incapable of serving as a leaving group in this regard in as much as the basicities of such halogen atoms are too low.

Such leaving groups may be prepared separately or in situ. For example, metallocene halides may be treated with alkylating agents such as dialkylaluminum alkoxides to generate the desired alkylmetallocene in situ. Reactions of this type are described for example in WO 95/10546.

Metallocene structures in this specification are to be interpreted broadly, and include structures containing 1, 2, 3 or 4 Cp or substituted Cp rings. Thus metallocenes suitable for use in this invention can be represented by the Formula I:

$$B_a Cp_b ML_c X_d \qquad (I)$$

where Cp independently in each occurrence is a cyclopentadienyl-moiety-containing group which typically has in the range of 5 to about 24 carbon atoms; B is a bridging group or ansa group that links two Cp groups together or alternatively carries an alternate coordinating group such as alkylaminosilylalkyl, silylamido, alkoxy, siloxy, aminosilylalkyl, or analogous monodentate hetero atom electron donating groups; M is a d- or f-block metal atom; each L is, independently, a leaving group that is bonded to the d- or f-block metal atom and is capable of forming a stable co-product on interaction with a proton from a hydroxyaluminoxane; X is a group other than a leaving group that is bonded to the d- or f-block metal atom;

a is 0 or 1; b is a whole integer from 1 to 3 (preferably 2); c is at least 2; d is 0 or 1. The sum of b, c, and d is sufficient to form a stable compound, and often is the coordination number of the d- or f-block metal atom.

Cp is, independently, a cyclopentadienyl, indenyl, fluorenyl or related group that can π-bond to the metal, or a hydrocarbyl-, halo-, halohydrocarbyl-, hydrocarbylmetalloid-, and/or halohydrocarbylmetalloid-substituted derivative thereof. Cp typically contains up to 75 non-hydrogen atoms. B, if present, is typically a silylene(—SiR$_2$—), benzo(C$_6$H$_4$<), substituted benzo, methylene(—CH$_2$—), substituted methylene, ethylene(—CH$_2$CH$_2$—), or substituted ethylene bridge. M is preferably a metal atom of Groups 4–6, and most preferably is a Group 4 metal atom, especially hafnium, and most especially zirconium. L can be a divalent substituent such as an alkylidene group, a cyclometallated hydrocarbyl group, or any other divalent chelating ligand, two loci of which are singly bonded to M to form a cyclic moiety which includes M as a member. In most cases L is methyl. X, if present, can be a leaving group or a non-leaving group, and thus can be a halogen atom, a hydrocarbyl group (alkyl, cycloalkyl, alkenyl, cycloalkenyl, aryl, aralkyl, etc.), hydrocarbyloxy, (alkoxy, aryloxy, etc.) siloxy, amino or substituted amino, hydride, acyloxy, triflate, and similar univalent groups that form stable metallocenes. The sum of b, c, and d is a whole number, and is often from 3–5. When M is a Group 4 metal or an actinide metal, and b is 2, the sum of c and d is 2, c being at least 1. When M is a Group 3 or Lanthanide metal, and b is 2, c is 1 and d is zero. When M is a Group 5 metal, and b is 2, the sum of c and d is 3, c being at least 2.

Also incorporated in this invention are compounds analogous to those of Formula I where one or more of the Cp groups are replaced by cyclic unsaturated charged groups isoelectronic with Cp, such as borabenzene or substituted borabenzene, azaborole or substituted azaborole, and various other isoelectronic Cp analogs. See for example Krishnamurti, et al., U.S. Pat. No. 5,554,775 and 5,756,611.

In one preferred group of metallocenes, b is 2, i.e., there are two cyclopentadienylmoiety containing groups in the molecule, and these two groups can be the same or they can be different from each other.

Another sub-group of useful metallocenes which can be used in the practice of this invention are metallocenes of the type described in WO 98/32776 published Jul. 30, 1998. These metallocenes are characterized in that one or more cyclopentadienyl groups in the metallocene are substituted by one or more polyatomic groups attached via a N, O, S, or P atom or by a carbon-to-carbon double bond. Examples of such substituents on the cyclopentadienyl ring include —OR, —SR, —NR$_2$, —CH=, —CR=, and —PR$_2$, where R can be the same or different and is a substituted or unsubstituted C$_1$–C$_{16}$ hydrocarbyl group, a tri-C$_1$–C$_8$ hydrocarbylsilyl group, a tri-C$_1$–C$_8$ hydrocarbyloxysilyl group, a mixed C$_1$–C$_8$ hydrocarbyl and C$_1$–C$_8$ hydrocarbyloxysilyl group, a tri-Cl–C$_8$ hydrocarbylgermyl group, a tri-C$_1$–C$_8$ hydrocarbyloxygermyl group, or a mixed C$_1$–C$_8$ hydrocarbyl and C$_1$–C$_8$ hydrocarbyloxygermyl group.

Examples of metallocenes to which this invention is applicable include such compounds as:

bis(methylcyclopentadienyl)titanium dimethyl;
bis(methylcyclopentadienyl)zirconium dimethyl;
bis(n-butylcyclopentadienyl)zirconium dimethyl;
bis(dimethylcyclopentadienyl)zirconium dimethyl;
bis(diethylcyclopentadienyl)zirconium dimethyl;
bis(methyl-n-butylcyclopentadienyl)zirconium dimethyl;
bis(n-propylcyclopentadienyl)zirconium dimethyl;
bis(2-propylcyclopentadienyl)zirconium dimethyl;
bis(methylethylcyclopentadienyl)zirconium dimethyl;
bis(indenyl)zirconium dimethyl;
bis(methylindenyl)zirconium dimethyl;
dimethylsilylenebis(indenyl)zirconium dimethyl;
dimethylsilylenebis(2-methylindenyl)zirconium dimethyl;
dimethylsilylenebis(2-ethylindenyl)zirconium dimethyl;
dimethylsilylenebis(2-methyl-4-phenylindenyl) zirconium dimethyl;
1,2-ethylenebis(indenyl)zirconium dimethyl;
1,2-ethylenebis(methylindenyl)zirconium dimethyl;
2,2-propylidenebis(cyclopentadienyl)(fluorenyl) zirconium dimethyl;
dimethylsilylenebis(6-phenylindenyl)zirconium dimethyl;
bis(methylindenyl)zirconium benzyl methyl;
ethylenebis[2-(tert-butyldimethylsiloxy)-1-indenyl] zirconium dimethyl;
dimethylsilylenebis(indenyl)chlorozirconium methyl;
5-(cyclopentadienyl)-5-(9-fluorenyl)1-hexene zirconium dimethyl;
dimethylsilylenebis(2-methylindenyl)hafnium dimethyl;
dimethylsilylenebis(2-ethylindenyl)hafnium dimethyl;
dimethylsilylenebis(2-methyl-4-phenylindenyl)hafnium dimethyl;
2,2-propylidenebis(cyclopentadienyl)(fluorenyl)hafnium dimethyl;
bis(9-fluorenyl)(methyl)(vinyl)silane zirconium dimethyl;
bis(9-fluorenyl)(methyl)(prop-2-enyl)silane zirconium dimethyl;
bis(9-fluorenyl)(methyl)(but-3-enyl)silane zirconium dimethyl;
bis(9-fluorenyl)(methyl)(hex-5-enyl)silane zirconium dimethyl;
bis(9-fluorenyl)(methyl)(oct-7-enyl)silane zirconium dimethyl;
(cyclopentadienyl)(1-allylindenyl)zirconium dimethyl;
bis(1-allylindenyl)zirconium dimethyl;
(9-(prop-2-enyl)fluorenyl)(cyclopentadienyl)zirconium dimethyl;
(9-(prop-2-enyl)fluorenyl)(pentamethylcyclopentadienyl) zirconium dimethyl;
bis(9-(prop-2-enyl)fluorenyl)zirconium dimethyl;
(9-(cyclopent-2-enyl)fluorenyl)(cyclopentadienyl) zirconium dimethyl;
bis(9-(cyclopent-2-enyl)(fluorenyl)zirconium dimethyl;
5-(2-methylcyclopentadienyl)-5(9-fluorenyl)-1-hexene zirconium dimethyl;
1-(9-fluorenyl)-1-(cyclopentadienyl)-1-(but-3-enyl)-1-(methyl)methane zirconium dimethyl;
5-(fluorenyl)-5-(cyclopentadienyl)-1-hexene hafnium dimethyl;
(9-fluorenyl)(1-allylindenyl)dimethylsilane zirconium dimethyl;
1-(2,7-di(alpha-methylvinyl)(9-fluorenyl)-1-(cyclopentadienyl)-1,1-dimethylmethane zirconium dimethyl;

1-(2,7-di(cyclohex-1-enyl)(9-fluorenyl))-1-(cyclopentadienyl)-1,1-methane zirconium dimethyl;

5-(cyclopentadienyl)-5-(9-fluorenyl)-1-hexene titanium dimethyl;

5-(cyclopentadienyl)-5-(9-fluorenyl)1-hexene titanium dimethyl;

bis(9-fluorenyl)(methyl)(vinyl)silane titanium dimethyl;

bis(9-fluorenyl)(methyl)(prop-2-enyl)silane titanium dimethyl;

bis(9-fluorenyl)(methyl)(but-3-enyl)silane titanium dimethyl;

bis(9-fluorenyl)(methyl)(hex-5-enyl)silane titanium dimethyl;

bis(9-fluorenyl)(methyl)(oct-7-enyl)silane titanium dimethyl;

(cyclopentadienyl)(1-allylindenyl) titanium dimethyl;

bis(1-allylindenyl)titanium dimethyl;

(9-(prop-2-enyl)fluorenyl)(cyclopentadienyl)hafnium dimethyl;

(9-(prop-2-enyl)fluorenyl)(pentamethylcyclopentadienyl) hafnium dimethyl;

bis(9-(prop-2-enyl)fluorenyl)hafnium dimethyl;

(9-(cyclopent-2-enyl)fluorenyl)(cyclopentadienyl) hafnium dimethyl;

bis(9-(cyclopent-2-enyl)(fluorenyl)hafnium dimethyl;

5-(2-methylcyclopentadienyl)-5(9-fluorenyl)-1-hexene hafnium dimethyl;

5-(fluorenyl)-5-(cyclopentadienyl)-1-octene hafnium dimethyl;

(9-fluorenyl)(1-allylindenyl)dimethylsilane hafnium dimethyl;

(tert-butylamido)dimethyl(tetramethylcyclopentadienyl) silane titanium(1,3-pentadiene);

(cyclopentadienyl)(9-fluorenyl)diphenylmethane zirconium dimethyl;

(cyclopentadienyl)(9-fluorenyl)diphenylmethane hafnium dimethyl;

dimethylsilanylene-bis(indenyl)thorium dimethyl;

dimethylsilanylene-bis(4,7-dimethyl-1-indenyl) zirconium dimethyl;

dimethylsilanylene-bis(indenyl)uranium dimethyl;

dimethylsilanylene-bis(2-methyl-4-ethyl-1-indenyl) zirconium dimethyl;

dimethylsilanylene-bis(2-methyl-4,5,6,7-tetrahydro-1-indenyl)zirconium dimethyl;

(tert-butylamido)dimethyl(tetramethyl-$\eta^5$-cyclopentadienyl)silane titanium dimethyl;

(tert-butylamido)dimethyl(tetramethyl-$\eta^5$-cyclopentadienyl)silane chromium dimethyl;

(tert-butylamido)dimethyl(tetramethyl-$\eta^5$-cyclopentadienyl)silane titanium dimethyl;

(phenylphosphido)dimethyl(tetramethyl-$\eta^5$-cyclopentadienyl)silane titanium dimethyl; and

[dimethylsilanediylbis(indenyl)]scandium methyl.

In many cases the metallocenes such as referred to above will exist as racemic mixtures, but pure enantiomeric forms or mixtures enriched in a given enantiomeric form can be used.

A feature of this invention is that not all metallocenes can produce compositions having the excellent catalytic activity possessed by the compositions of this invention. For example, in the absence of a separate metal alkyl compound, bis(cyclopentadienyl)dichlorides of Zr cannot produce the compositions of this invention because the chloride atoms are not capable of serving as leaving groups under the conditions used in forming the compositions of this invention. Thus on the basis of the state of present knowledge, in order to practice this invention, it is desirable to perform preliminary tests with any given previously untested metallocene to determine catalytic activity of the product of reaction with a hydroxyaluminoxane. In conducting such preliminary tests, use of the procedures and reaction conditions of the Examples presented hereinafter, or suitable adaptations thereof, is recommended.

In another embodiment of this invention, contrary to that which was previously known, it now surprisingly has been found that rac-ethylenebis(1-indenyl)zirconium dimethyl also can be used to produce a polymerization catalyst composition of this invention which exhibits catalytic activity. Example 15 hereinafter illustrates the preparation and use of this catalyst composition as an olefin polymerization catalyst.

Reaction Conditions

To produce the catalytically active catalyst compositions of this invention the reactants, the d- or f-block metal compound, and the hydroxyaluminoxane that has either been freshly prepared or stored at low temperature (e.g., −10° C. or below) are brought together preferably in solution form or on a support. The reaction between the hydroxy group and the bond between the leaving group and the d- or f-block metal is stoichiometric and thus the proportions used should be approximately equimolar. The temperature of the reaction mixture is kept in the range of about −78 to about 160° C. and preferably in the range of about 15 to about 30° C. The reaction is conducted under an inert atmosphere and in an inert environment such as in an anhydrous solvent medium. Reaction times are short, typically within four hours. When the catalyst composition is to be in supported form on a catalyst support or carrier, the suitably dried, essentially hydrate-free support can be included in the reaction mixture. However, it is possible to add the catalyst to the support after the catalyst composition has been formed.

When substituting for the hydroxyaluminoxane reactant in these reactions the composition of matter of this invention which is in the form of either a gelatinous composition or a solid composition formed from the gelatinous composition, or a mixture of both, the reaction conditions for producing the active catalyst compositions will be the same as those taught in the preceding paragraph. The use of these co-catalyst compositions of matter in forming the active catalyst composition are preferred over unsupported hydroxyaluminoxane, since they provide a more stable reactant (the hydroxyaluminoxane gel and/or gel-derived solid compositions) in terms of OH-decay as compared to unsupported hydroxyaluminoxane, which in turn enables the use of lower amounts (on a molar basis) of the hydroxyaluminoxane gel and/or gel-derived solid composition to obtain at least the same level of activation.

It should also be noted that, just as in the formation of the co-catalyst compositions from hydroxyaluminoxane and a treating agent, the catalysts may be formed by bringing together the metal compound and the co-catalyst composition without isolating the gelatinous co-catalyst from solution. Thus, for example, the metal compound may be mixed with the co-catalyst composition in the same reaction vessel or zone in which the co-catalyst composition is formed, and whether the co-catalyst is formed by bringing together a starting hydroxyaluminoxane and a treating agent, or by bringing together a starting aluminum alkyl and water source (e.g., water) under gelatinous co-catalyst composition forming conditions. In other words, the metal compound may be brought together with a mixture in which the co-catalyst may be formed in order to form the activated catalyst composition in situ, whereupon the catalyst composition may be isolated and used or stored for later use as a polymerization catalyst. The reaction conditions for in situ formation of the active catalyst compositions should be the same as those taught above generally for the formation of the active catalyst compositions. Accordingly, another embodiment of this invention is the process which comprises bringing together, in an inert solvent, an aluminum alkyl and a water source to form a first mixture in which a gelatinous composition is formed, and then bringing the first mixture together with the d- or f-block metal compound to form a second mixture in which an activated polymerization catalyst is formed. If desired, the activated catalyst then may be isolated from the second mixture. This embodiment presents a particularly economical way of producing the desired catalyst in a highly stable form.

Recovery of the Active Catalyst Compositions

Typically the active catalyst composition can be recovered from the reaction mixture in which it was formed simply by use of a known physical separation procedure. Since the reaction involved in the formation of the product preferably uses a metallocene having one or two methyl groups whereby gaseous methane is formed as the co-product, the metal-containing catalyst product is usually in a reaction mixture composed almost entirely of the desired catalyst composition and the solvent used. This renders the recovery procedure quite facile. For example, where the product is in solution in the reaction mixture, the solvent can be removed by stripping off the solvent under reduced pressure and at moderately elevated temperature. Often the residual product recovered in this manner is of sufficient purity that further purification is not required. In the event the product is in the form of solids which precipitate from the solvent, or which are caused to precipitate from the solution by the addition of a suitable non-solvent, physical solid-liquid separation procedures such as filtration, centrifugation, and/or decantation can be employed. The product recovered in this manner is usually of sufficient purity that further purification is not required. Whatever the method of recovery used, if further purification is needed or desired, conventional purification steps, such as crystallization can be used.

The product need not be recovered or isolated directly from the liquid reaction medium in which it was prepared. Instead, it can be transferred to another solvent, for example, by use of a solvent extraction procedure or a solvent swap procedure whereby the product is removed from the liquid phase in which it was produced and is thus dissolved in a different solvent. Although unnecessary, this new solution can be subjected to still another solvent extraction, or solvent swap, as many times as desired, recognizing of course that the longer the product remains in solution the greater the opportunity for product degradation to occur. In any case referred to in this paragraph, the catalytically active product is recovered or isolated from a solution other than the liquid phase in which it was produced, and is maintained in undissolved condition under dry, anhydrous conditions.

Storage of Recovered Active Catalyst Compositions

The recovered catalyst compositions of this invention can be stored in any suitable air-tight container either under vacuum or under an atmosphere of anhydrous inert gas, such as nitrogen, helium, argon, or the like. To protect against possible light-induced degradation, the container is preferably opaque or rendered opaque toward light transmission and/or the package containing the catalyst composition is kept in a suitable dark storage area. Likewise it is desirable to store the product in locations that will not become excessively hot. Exposure to storage temperatures of up to about 30° C. typically will cause no material loss in activity, but naturally the effect of temperatures likely to be encountered during storage should be determined for any given catalyst where such information has not previously been ascertained.

The length of time during which the recovered active catalyst composition is stored can be as short as a minute or less. For example, the active catalyst composition could be produced in an appropriate amount at the site of the polymerization and immediately upon isolation could be directly transferred to the polymerization reaction vessel. The storage period in such case could be very short, namely the time between isolation of the active catalyst composition and commencement of its use as the catalyst in the polymerization. On the other hand, the storage period can be substantially longer provided that the storage occurs under the appropriate conditions at all times during the storage. For example, the active catalyst composition could be produced, placed in a suitable air-tight, moisture-resistant vessel or container under a dry, anhydrous atmosphere promptly after its isolation, and then maintained in inventory in a suitable air-tight, moisture-resistant vessel or container under a dry, anhydrous atmosphere, all at the site of its manufacture, and with these steps being conducted such that the amount of exposure to air or moisture, if any, is kept at all times to such a minimal amount as not to adversely affect the activity of the catalyst composition. All or a portion of such stored active catalyst composition could then be shipped under these same conditions to another site, typically the site where its use as a polymerization catalyst is to take place. And after reaching the site where the composition is to be used as a catalyst, the composition could then again be kept in inventory under the same or substantially the same type of suitable storage conditions at that site until portions of the catalyst composition are put to use as a catalyst. In such a case the overall storage period could be very long, e.g., as long as the particular catalyst composition retains suitable catalytic activity. Thus the period of storage is discretionary and is subject to no numerical limitation as it can depend on such factors as the extent of care exercised in the various steps to which the stored product is subjected during storage, the conditions existing or occurring during the storage, and so on. Thus as a practical matter the period of time of the storage can be the period of time during which the catalyst does not lose its activity or effectiveness when used as a polymerization catalyst.

The catalyst compositions of this invention can be stored in isolated form, or in various other undissolved forms. For example, after recovery, the active catalyst composition can be mixed under dry, anhydrous conditions with dry inert materials such as calcined particulate or powdery silica, alumina, silica-alumina, clay, montmorillonite, diatomaceous earth, or like substance, and the resultant dry blend can be stored under appropriate dry, anhydrous conditions. Similarly, after recovery, the active catalyst composition can be mixed under dry, anhydrous conditions with other kinds of dry inert materials such as chopped glass fibers, glass beads, carbon fibers, metal whiskers, metal powders, and/or other materials commonly used as reinforcing fillers for polymers, and the resultant blends can then be stored under appropriate dry, anhydrous conditions. In a preferred embodiment, after recovery, the active catalyst composition is supported on a dry catalyst support material such as calcined silica, calcined silica-alumina, calcined alumina, particulate polyethylene, particulate polypropylene, or other polyolefin homopolymer or copolymer under anhydrous air-free conditions using known technology, and the resultant supported catalyst composition is then stored under appropriate dry, anhydrous conditions. In case anyone needs to be told what "appropriate conditions" are, they include not exposing the stored catalyst composition to such high temperatures as would cause destruction of the catalyst or its catalytic activity, and not exposing the stored catalyst to light wave energy or other forms of radiation of such type or magnitude as would cause destruction of the catalyst or its catalytic activity. Here again, this disclosure as any patent disclosure, should be read with at least a little common sense, rather than with legalistic word play in mind.

The catalyst compositions of this invention are particularly stable, as they typically will be able to be maintained in a dry state under anhydrous or substantially anhydrous conditions and at a temperature in the range of about 5 to about 70° C., more preferably in the range of about 10 to about 60° C., and most preferably in the range of about 15 to about 35° C., for a period of time of at least about 24 hours, more preferably for at least about 48 hours, and most preferably at least about 72 hours, without losing fifty percent (50%) or more of its catalytic activity. It should be appreciated that such catalytic activity would be measured in terms of grams of polymer per gram of catalyst composition per hour, samples being compared using identical polymerization reaction conditions.

Polymerization Processes Using Catalysts of this Invention

The catalyst compositions of this invention can be used in solution or, optionally, deposited on a solid support. When used in solution polymerization, the solvent can be, where applicable, a large excess quantity of the liquid olefinic monomer. Typically, however, an ancillary inert solvent, typically a liquid paraffinic or aromatic hydrocarbon solvent is used, such as heptane, isooctane, decane, toluene, xylene, ethylbenzene, mesitylene, or mixtures of liquid paraffinic hydrocarbons and/or liquid aromatic hydrocarbons. When the catalyst compositions of this invention are supported on a carrier, the solid support or carrier can be any suitable particulate solid, and particularly a porous support such as talc, zeolites, or inorganic oxides, or resinous support material such as polyolefins. Preferably, the support material is an inorganic oxide in finely divided form.

Suitable inorganic oxide support materials which are desirably employed include metal oxides such as silica, alumina, silica-alumina and mixtures thereof. Other inorganic oxides that may be employed either alone or in combination with the silica, alumina or silica-alumina are magnesia, titania, zirconia, and like metal oxides. Other suitable support materials are finely divided polyolefins such as finely divided polyethylene.

Polymers can be produced pursuant to this invention by homopolymerization of polymerizable olefins, typically 1-olefins (also known as α-olefins) such as ethylene, propylene, 1-butene, or copolymerization of two or more copolymerizable monomers, at least one of which is typically a 1-olefin. The other monomer(s) used in forming such copolymers can be one or more different 1-olefins and/or a diolefin, and/or a polymerizable acetylenic monomer. Olefins that can be polymerized in the presence of the catalysts of this invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexa-decene, and 1-octadecene. Other suitable monomers for producing homopolymers and copolymers include styrenic monomers, e.g., styrene, ar-methylstyrenes, alpha-methylstyrene, ar-dimethylstyrenes, ar-ethylstyrene, 4-tert-butylstyrene, and vinylnaphthalene. Still other suitable monomers include polycyclic monomers. Illustrative examples of suitable polycyclic monomers include 2-norbornene, 5-methyl-2-norbornene, 5-hexyl-2-norbornene, 5-decyl-2-norbornene, 5-phenyl-2-norbornene, 5-naphthyl-2-norbornene, 5-ethylidene-2-norbornene, vinylnorbornene, dicyclopentadiene, dihydrodicyclopentadiene, tetracyclododecene, methyltetracyclododecene, tetracyclododecadiene, dimethyltetracyclododecene, ethyltetracyclododecene, ethylidenyl tetracyclododecene, phenyltetracyclododecene, trimers of cyclopentadiene (e.g., symmetrical and asymmetrical trimers). Copolymers based on use of isobutylene as one of the monomers can also be prepared. Normally, the hydrocarbon monomers used, such as 1-olefins, diolefins and/or acetylene monomers, will contain up to about 10 carbon atoms per molecule. Preferred 1-olefin monomers for use in the process include ethylene, propylene, 1-butene, 3-methyl-1-butene, 4-methyl-1-pentene, 1-hexene, and 1-octene. It is particularly preferred to use catalysts of this invention in the polymerization of ethylene, or propylene, or ethylene and at least one $C_3$–$C_8$ 1-olefin copolymerizable with ethylene. Typical diolefin monomers which can be used to form terpolymers with ethylene and propylene include butadiene, hexadiene, norbornadiene, and similar copolymerizable diene hydrocarbons. 1-Heptyne and 1-octyne are illustrative of suitable acetylenic monomers which can be used.

Polymerization of ethylene or copolymerization with ethylene and an α-olefin having 3 to 10 carbon atoms may be performed in either the gas or liquid phase (e.g. in a diluent, such as toluene, or heptane). The polymerization can be conducted at conventional temperatures (e.g., 0° to 120° C.) and pressures (e.g., ambient to 50 kg/cm$^2$) using conventional procedures as to molecular weight regulations and the like.

The heterogeneous catalysts of this invention can be used in polymerizations conducted as slurry processes or as gas phase processes. By "slurry" is meant that the particulate catalyst is used as a slurry or dispersion in a suitable liquid reaction medium which may be composed of one or more ancillary solvents (e.g., liquid aromatic hydrocarbons, etc.) or an excess amount of liquid monomer to be polymerized in bulk. Generally speaking, these polymerizations are conducted at one or more temperatures in the range of about 0 to about 160° C., and under atmospheric, subatmospheric, or superatmospheric conditions. Conventional polymerization adjuvants, such as hydrogen, may be employed if desired. Preferably polymerizations conducted in a liquid reaction medium containing a slurry or dispersion of a catalyst of this invention are conducted at temperatures in the range of about 40 to about 110° C. Typical liquid diluents for such processes include hexane, toluene, and like materials. Typically, when conducting gas phase polymerizations, superatmospheric pressures are used, and the reactions are conducted at temperatures in the range of about 50 to about 160° C. These gas phase polymerizations can be performed in a stirred or fluidized bed of catalyst in a pressure vessel adapted to permit the separation of product particles from unreacted gases. Thermostated ethylene, comonomer, hydrogen and an inert diluent gas such as nitrogen can be introduced or recirculated to maintain the particles at the desired polymerization reaction temperature. An aluminum alkyl such as triethylaluminum may be added as a scavenger of water, oxygen and other impurities. In such cases the aluminum alkyl is preferably employed as a solution in a suitable dry liquid hydrocarbon solvent such as toluene or xylene. Concentrations of such solutions in the range of about $5 \times 10^{-5}$ molar are conveniently used. But solutions of greater or lesser concentrations can be used, if desired. Polymer product can be withdrawn continuously or semi-continuously at a rate that maintains a constant product inventory in the reactor.

The catalyst compositions of this invention can also be used along with small amounts of hydrocarbylborane compounds such as triethylborane, tripropylborane, tributylborane, tri-sec-butylborane. When so used, molar Al/B ratios in the range of about 1/1 to about 1/500 can be used.

Because of the high activity and productivity of the catalysts of this invention, the catalyst levels used in olefin polymerizations can be less than previously used in typical olefin polymerizations conducted on an equivalent scale. In general, the polymerizations and copolymerizations conducted pursuant to this invention are carried out using a catalytically effective amount of a novel catalyst composition of this invention, which amount may be varied depending upon such factors such as the type of polymerization being conducted, the polymerization conditions being used, and the type of reaction equipment in which the polymerization is being conducted. In many cases, the amount of the catalyst of this invention used will be such as to provide in the range of about 0.000001 to about 0.01 percent by weight of d- or f-block metal based on the weight of the monomer(s) being polymerized.

After polymerization and deactivation of the catalyst in a conventional manner, the product polymer can be recovered from the polymerization reactor by any suitable means. When conducting the process with a slurry or dispersion of the catalyst in a liquid medium the product typically is recovered by a physical separation technique (e.g. decantation, etc.). The recovered polymer is usually washed with one or more suitably volatile solvents to remove residual polymerization solvent or other impurities, and then dried, typically under reduced pressure with or without addition of heat. When conducting the process as a gas phase polymerization, the product after removal from the gas phase reactor is typically freed of residual monomer by means of a nitrogen purge, and often can be used without further catalyst deactivation or catalyst removal.

When preparing polymers pursuant to this invention conditions may be used for preparing unimodal or multimodal polymer types. For example, mixtures of catalysts of this invention formed from two or more different metallocenes having different propagation and termination rate constants for ethylene polymerizations can be used in preparing polymers having broad molecular weight distributions of the multimodal type.

Experimental Section

Figure 3:
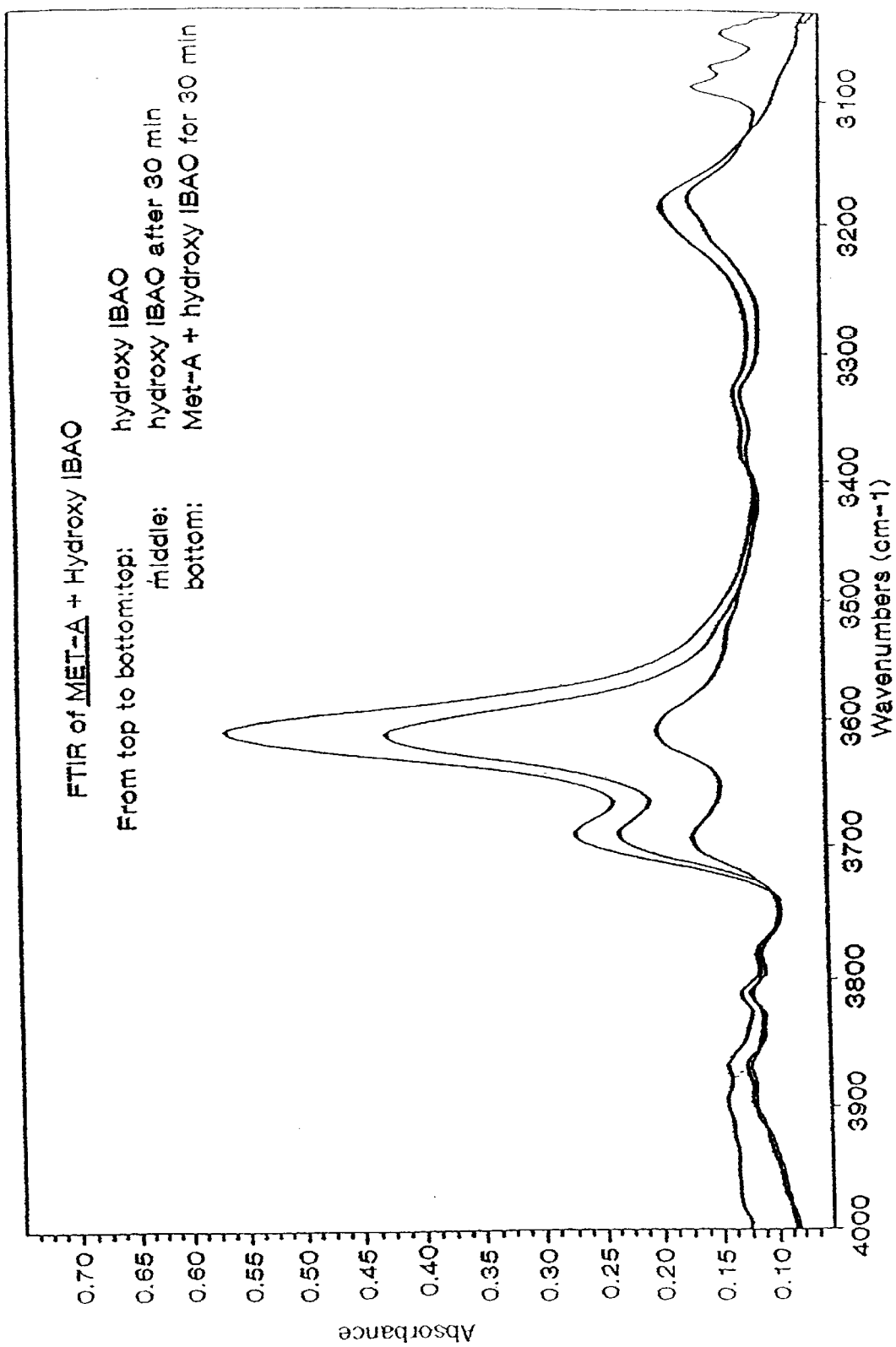
FIG. 3 is a superimposed series of infrared spectra, the top spectrum being that of a fresh HO-IBAO, the middle spectrum being that of the same HO-IBAO but taken 30 minutes later, and the bottom spectrum being that a catalyst composition of this invention formed from the reaction between rac-dimethylsilylbis(2-methylindenyl)zirconium dimethyl (MET-A) and HO-IBAO showing that the activation of a metallocene having a suitable leaving group is accompanied by a rapid loss of hydroxyl groups, consistent with HO-IBAO functioning as a Brønsted acid in metallocene activation.

The following Examples are presented for purposes of illustration and not limitation. All operations of these Examples were carried out under nitrogen either in a drybox with below 1 ppm oxygen or using standard Schlenk line techniques. Methylaluminoxane (MAO), triethylaluminum (TEA) and triisobutylaluminum (TIBA), were commercial products of Albemarle Corporation and used as received. Reagents benzylmagnesium chloride and MeLi with LiBr were purchased from Aldrich and used as received. Toluene, ethylene, propylene, and nitrogen used in the polymerization reactions were purified by passing through a series of three cylinders: molecular sieves, Oxyclear oxygen absorbent, and alumina. Ethylene and propylene were polymer grade from Matheson. Toluene for catalyst preparation and spectroscopy studies was Aldrich anhydrous grade and was distilled from sodium/benzophenone ketyl. Hexane was Aldrich anhydrous grade and stored over Na/K alloy. The metallocenes used in these Examples were prepared according to procedures given in the literature. Thus $Cp_2ZrMe_2$ was prepared using the method of Samuel, et al., *J. Am. Chem. Soc.*, 1973, 95, 6263; rac-dimethylsilylbis(2-methyl-1-indenyl)zirconium dichloride using the method of Spaleck, et al., *Angew. Chem., Int. Ed. Engl.*, 1992,31,1347, and Winter, et al. U.S. Pat. No. 5,145,819; and bis(1-methyl-3-n-butyl-cyclopentadienyl)zirconium dichloride using the method of Lee, et al., Canadian Pat. No. 2,164,914, July 1996. The infrared spectra in FIGS. 1, 2 and 3 were recorded on a Nicolet Magna-IR 750 spectrometer with 32 scans and 2 cm−1 resolution using 0.5 mm NaCl cells. The absorption of hexane was compensated by subtraction with a reference hexane spectrum acquired from the same cell. The UV-Vis spectra were recorded in the 290–700 nm region on a Varian Cary 3E spectrometer. Quartz cuvettes of 1 cm pathlength were used. The FT-IR spectrum of HO-IBAO(1.2) in FIG. 8 was recorded by a Nicolet Magna 560 FTIR bench with a Nic-Plan infrared microscope using 64 scans and 8 cm−1 resolution. Diffuse reflectance infrared Fourier transform spectroscopy (DRIFTS) use a Nicolet Magna 750 FTIR bench equipped with a "Collector" diffuse reflectance accessory from Spectra-Tech with a high temperature/high pressure sample chamber. The DRIFTS spectra (FIG. 9) were obtained at 4 cm−1 resolution and 128 scans. The molecular weight and molecular weight distribution were determined by gel permeation chromatography which incorporated three different modes of detection including differential refractive index (Polymer Labs), laser light scattering (Precision Detectors) and differential pressure viscometry (Viscotek Corporation). The chromatographic instrument was a Polymer Labs 210 using 1,2,4-trichlorobenzene as the eluting solvent at 150° C. A series of linear mixed bed GPC columns were used to perform the separation and the data was collected and analyzed using Viscotek's TriSEC software package. The samples were dissolved in the trichlorobenzene for 2–4 hours at 150° C. at a concentration of approximately 2000 ppm. MFI, melt flow index, was determined by the ASTM D1238 method.

EXAMPLE 1

Rac-Dimethylsilylbis(2-methylindenyl)zirconium Dimethyl (MET-A)

Rac-dimethylsilylbis(2-methylindenyl)zirconium dichloride (5.03 g, 10.55 mmol) was suspended in 100 g of toluene. The orange slurry was heated in an oil bath to 40° C. Most of the orange-yellow metallocene remained undissolved. MeLi/LiBr(5.87 wt % in ether, 7.78 g) was added dropwise over two hours. The solution became amber/yellow and the solids lightened. The reaction was allowed to cool to ambient temperature and stir overnight. Analysis of the reaction showed 9.3 mol % of mono-methyl intermediates. Additional aliquots of MeLi/LiBr(1.66 g) were added dropwise until the monomethyl intermediates were reduced to less than two mol %. Approximately a quarter of the solvent was removed in vacuo and then the lithium salts were filtered on a medium frit and washed with 20 mL of toluene. The combined filtrates were concentrated in vacuo. A yellow crystalline solid formed. The slurry was cooled to −20° C. The yellow crystals were filtered on a coarse frit. After drying in vacuo, the yield of rac-dimethylsilyl-bis(2-methylindenyl)zirconium dimethyl was 3.20 g (70%).

EXAMPLE 2

Bis(1-Butyl-3-methylcyclopentadienyl)zirconium Dimethyl (MET-B)

Bis(1-butyl-3-methylcyclopentadienyl)zirconium dichloride (2.71 g, 6.26 mmol)was dissolved in 21.4 g of toluene. Low-halide MeLi (~1.5 M in ether, 8.0 mL) was added dropwise at ambient temperature. A white solid formed immediately. The reaction was allowed to stir for 1.5 hours. Analysis of the reaction showed 3.5 mol % of mono-methyl intermediate. An additional aliquot of MeLi (0.4 mL) was then added to consume the monomethyl intermediate. After stirring overnight, the supernatant liquid was reanalyzed to verify that the reaction was complete. The slurry was filtered on a medium flit and the solvent was removed in vacuo. A light yellow liquid of bis(1-butyl-3-methyl-cyclopentadienyl)zirconium dimethyl remained (2.13 g, 87% yield).

EXAMPLE 3

Synthesis of Hydroxyisobutylaluminoxane (HO-IBAO)

The reaction was carried out in a 1-L, three-necked, round-bottomed Morton flask equipped with a thermometer, an outlet connected to a Schlenk line, and a rubber septum through which water was added via a syringe needle. To this flask containing a solution of triisobutylaluminum (98.4 g, 492.4 mmol) in hexane (276.4 g) with vigorous magnetic stirring was added degassed water (8.85 g, 491.4 mmol) using a syringe pump over a period of 65 minutes. The temperature was maintained at between −5 and 0° C. by applying a dry ice bath (without acetone) and by adjusting water addition speed. After the water addition was complete, the solution was stirred for an additional ten minutes (or until the exothermic reaction subsided, which usually lasts about 5–10 minutes after completion of water addition), stripped of dissolved isobutane and some hexane under vacuum at a temperature somewhat below ambient, transferred, and stored in a −10° C. freezer in a drybox. The solution weighed 252.2 g and was determined by analysis to have a wt % Al of 5.15.

EXAMPLE 4

Synthesis of Deuteroxyisobutylaluminoxane (DO-IBAO)

The procedure of Example 3 was repeated with the exception that an equivalent amount of $D_2O$ was used in place of the water and the operation was conducted with similar amounts of the reactants.

EXAMPLE 5

Characterization of HO-IBAO by IR-Spectroscopy

The presence of hydroxyl groups in the product solution of Example 3 was indicated by an infrared spectrum (see FIG. 1) taken the next day. Initially, there are two types of hydroxyl groups detected at 3615 $cm^{-1}$ (major) and 3695 $cm^{-1}$ (minor), respectively. At room temperature, both are unstable particularly the major one. The stability study was carried out with another reaction solution in hexane (Al wt %=3.55, $H_2O$/Al=1.00). The liquid cuvette was left in the IR chamber at ambient temperature and spectra were recorded at the indicated intervals (see FIG. 2). The last spectrum taken after two days at ambient temperature, revealed possibly two additional OH frequencies at 3597 $cm^{-1}$ and 3533 $cm^{-1}$. The stability of the hydroxyl groups depends on a number of factors. For instance, the hydroxyl groups can be preserved for a much longer time if the solution is kept at a lower temperature, or if added tetrahydrofuran which stabilizes the hydroxyls both by forming hydrogen-bonds, and by coordinating to aluminum sites; or by using a higher hydrolysis ratio (hydroxyls are more stable in IBAO of water/Al=1.00 than in IBAO of water/Al=0.90).

As indicated by Example 4, the hydroxyl groups can be replaced by deuteroxy groups by hydrolyzing TIBA with $D_2O$. A new IR band assignable to OD stretching appeared at 2665 $cm^{-1}$ corresponding to the 3615 $cm^{-1}$ band for OH stretching (the corresponding OD band for the 3695 $cm^{-1}$ stretching is not seen, presumably obscured by large C-H bands nearby). The ratio of two frequencies ($n_{OH}/n_{OD}$=1.356) indicates that this OH or OD group is free or not engaged in any intra or intermolecular hydrogen bonding (the theoretical value is 1.35 which falls systematically as the strengths of the hydrogen bond increases; see L. J. Bellamy, *The Infrared Spectra of Complex Molecules*, Volume Two, Second Edition, 1980, page 244, Chapman and Hall). Deuterated isobutane, $(CH_3)_2CHCH_2D$, a by-product of the hydrolysis reaction, was also detected by IR as two equally intense bands at 2179 $cm^{-1}$ and 2171 $cm^{-1}$, respectively.

To enable correlation between IR absorbance and hydroxy content of HO-IBAO, a quantitative determination of hydroxy content was performed (Example 6). In the absence of a model compound with known hydroxy content, IR spectroscopy provides only qualitative information.

EXAMPLE 6

Quantification of Hydroxy Content in HO-IBAO, Benzyl Grimnard Method

To a cold, vigorously stirred HO-IBAO solution (5.52 g solution, 10 mmol Al) with a 4.89 wt % Al and an IR absorbance of 0.557 for the 3616 $cm^{-1}$ band was added a 2-M solution of benzylmagnesium chloride in THF (2.0 ml, 4 mmol). The mixture quickly reacted becoming two layers and was stirred at ambient temperature for 90 minutes. After that, the resulting suspension was vacuum distilled at temperatures up to 50° C. over one hour and all volatiles were trapped in a flask cooled by a liquid nitrogen bath. The amount of toluene in the collected liquid was determined by GC (with a known amount of pentadecane added as an internal reference) to be 0.66 mmol, which corresponds to 6.6 OH groups for every 100 Al atoms.

The mechanism as depicted in Equation (2) above was proved by the use of two different experiments, one involving deuterium labeling and GC-mass spectrographic analysis (Examples 7 and 8), and the other infra-red analysis (Example 7).

EXAMPLE 7

Verification of Novel Metallocene Activation Mechanism: HO-IBAO Functions As a Brønsted Acid Use of deuterium-Labeled Reactant (DO-IBAO) with Unbridged Metallocene. Into a 30-mL round-bottomed flask containing a cold solution of deuteroxyisobutylaluminoxane (DO-IBAO) (OD stretching at 2665 cm$^{-1}$, about 5–7 OD for every 100 Al) (3.31 wt % Al, 9.26 g solution, 11.4 mmol Al) prepared by hydrolyzing the TIBA with D$_2$O was added solid bis(cyclopentadienyl)zirconium dimethyl (Cp$_2$ZrMe$_2$) (33 mg, 0.13 mmol). The flask was immediately closed with a gas tight septum to prevent escape of any gaseous products. The volume of the solution was ca. 15 mL which left about another 15 mL of headspace in the flask. It took about 2–3 minutes for the metallocene solids to dissolve completely to give a light yellow solution. After stirring for 85 minutes at ambient temperature, a gaseous sample withdrawn from the head space of the flask was subjected to GC-Mass Spec analysis which showed a composition of 9.1 mol % CH$_3$D and 90.9 mol % N$_2$. In other words, 1.37 mL of the 15-mL headspace was CH$_3$D, which corresponds to 43% of the theoretical amount predicted by the reaction of Equation (2) above. The amount of CH$_3$D remained dissolved in the solution was not determined. (In fact, if the solution was cooled to −10 to −20° C., CH$_3$D in the headspace became too little to be detectable by GC-Mass Spec).

EXAMPLE 8

Verification of Novel Metallocene Activation Mechanism: HO-IBAO Functions As a Brønsted Acid Use of Deuterium-Labeled Reactant (DO-IBAO) with Bridged Metallocene. This reaction was carried out analogously to Example 7 above except that the reactants were rac-dimethylsilylbis(2-methyl-1-indenyl)zirconium dimethyl (45 mg, 0.103 mmol) and DO-IBAO (12.23 g, 15.0 mmol Al) and the flask contained about 19-mL of solution and 11-mL of headspace. The GC-Mass Spec analysis showed a 4.8 mol % of CH$_3$D in the headspace, which corresponds to 21% of the theoretical amount. The lower percentage reflects the fact that the flask had less headspace and more solution volume for CH$_3$D to dissolve in.

EXAMPLE 9

Verification of Novel Metallocene Activation Mechanism: HO-IBAO Functions As a Brønsted Acid Use of Infra-Red Analysis of Product from HO-IBAO and a Metallocene. To a cold, freshly prepared HO-IBAO(3.0 mmol Al, IR spectrum shown in FIG. 4(a)) in hexane was added solid dimethylsilylbis(methylindenyl)zirconium dimethyl (0.1 mmol, Al/Zr=30). After stirring at ambient temperature for 30 minutes, the resulting deep red-brown solution was taken a IR spectrum shown in FIG. 4(c). Separately, another portion of the same cold HO-IBAO solution was allowed to stand at ambient temperature for 30 minutes and its IR spectrum was taken immediately thereafter (shown in FIG. 4(b). It is clear from this set of three spectra that the reaction between HO-IBAO and the metallocene results in a rapid disappearance of the hydroxyl groups in IBAO, which cannot be accounted for by the slower self-consumption during the same period.

EXAMPLE 10

Figure 4:
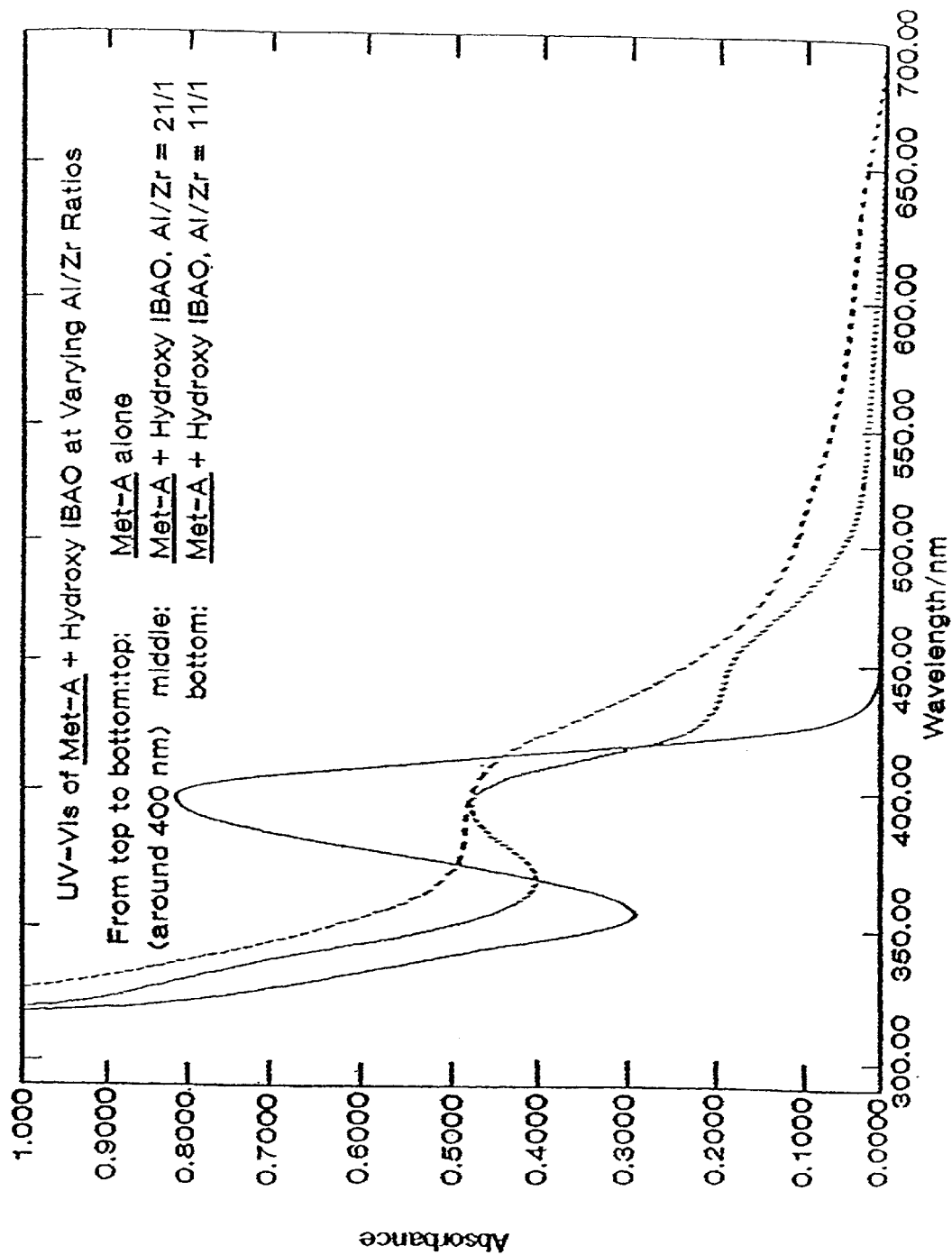
FIG. 4 are superimposed UV-Vis spectra, the top spectrum being that of MET-A, the middle spectrum being that of a catalyst composition of this invention having an Al/Zr ratio of 21/1 formed from the reaction between MET-A and HO-IBAO, and the bottom spectrum being that of a catalyst composition of this invention having an Al/Zr ratio of 11/1 formed from the reaction between MET-A and HO-IBAO.

UV-Vis Spectra of rac-dimethylsilylbis(2-methylindenyl)zirconium dimethyl+Hydroxy IBAO With Varying Al/Zr Ratios The reaction between hydroxy IBAO and methylated metallocene can be readily monitored by UV-Vis. It has been reported that the ligand-to-metal charge transfer (LMCT) bands undergo a characteristic bathochromic shift (shorter to longer wavelength) upon converting from a neutral metallocene (catalyst precursor) to a metallocenium cation (active catalyst) by an activator (Siedle, et al., *Macromol. Symp.*, 1995, 89, 299; Pieters, et al., *Macroinol. Rapid Commun.*, 1995, 16, 463). For rac-dimethylsilylbis(2-methyl-indenyl)zirconium dimethyl, an LMCT band (see FIG. 4-solid) appearing at 394 nm ($\lambda_{max}$, 4710 M$^{-1}$ cm$^{-1}$) serves as a convenient probe to measure the progress of the activation reaction. As shown in FIG. 4-dotted, the more hydroxy IBAO is used, the more the starting metallocene is consumed and the more adsorption is observed in the longer wavelength region. It is clear from the spectra that an Al/Zr ratio of 21 is almost enough to activate all of the metallocene.

Figure 5:
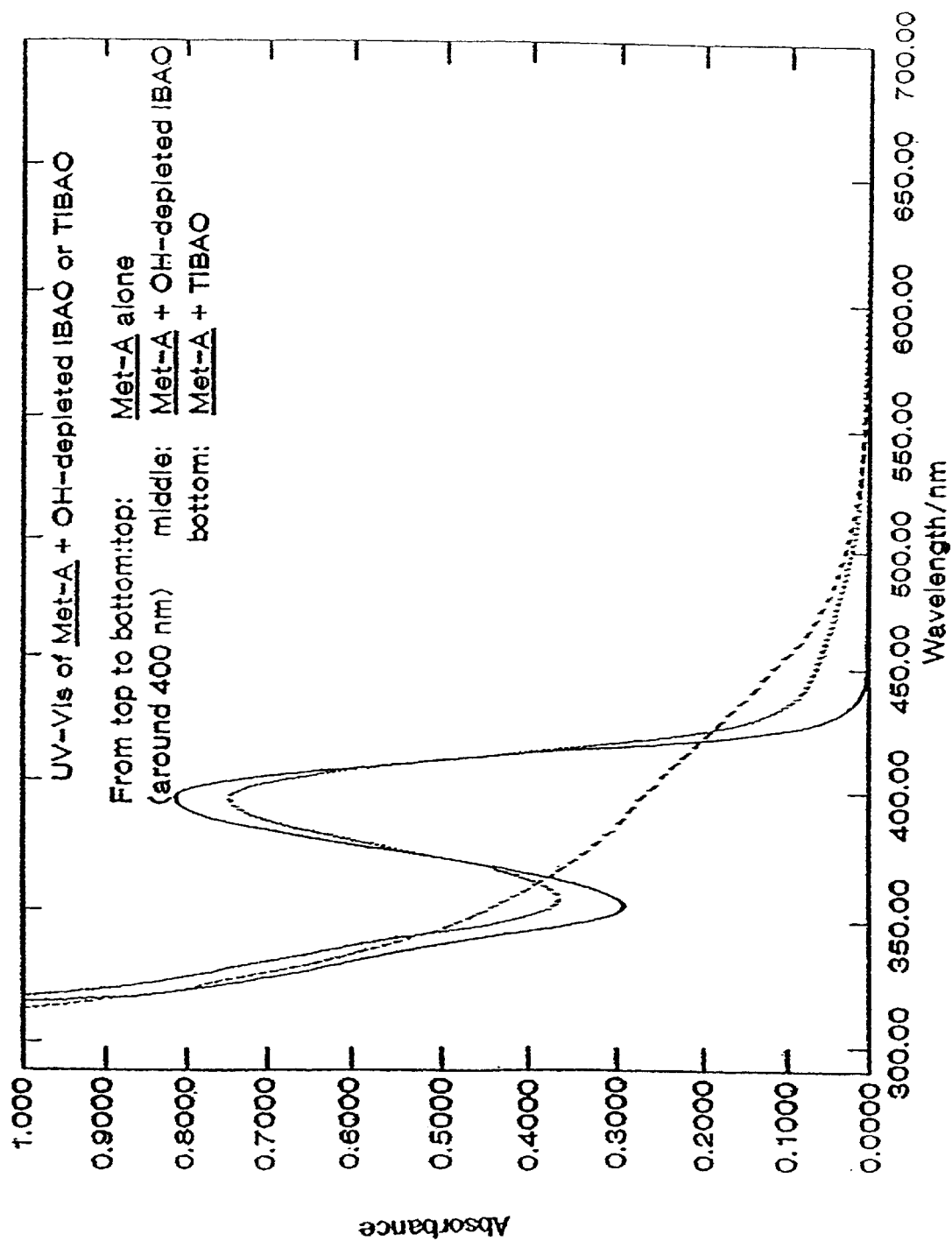
FIG. 5 are superimposed UV-Vis spectra, the top spectrum being that of MET-A, the middle spectrum being that of a composition formed from MET-A and isobutylaluminoxane (IBAO) that resulted from loss or depletion of hydroxyl groups from IBAO, and the bottom spectrum being that of tetraisobutyldialuminoxane (TIBAO).
Figure 6:
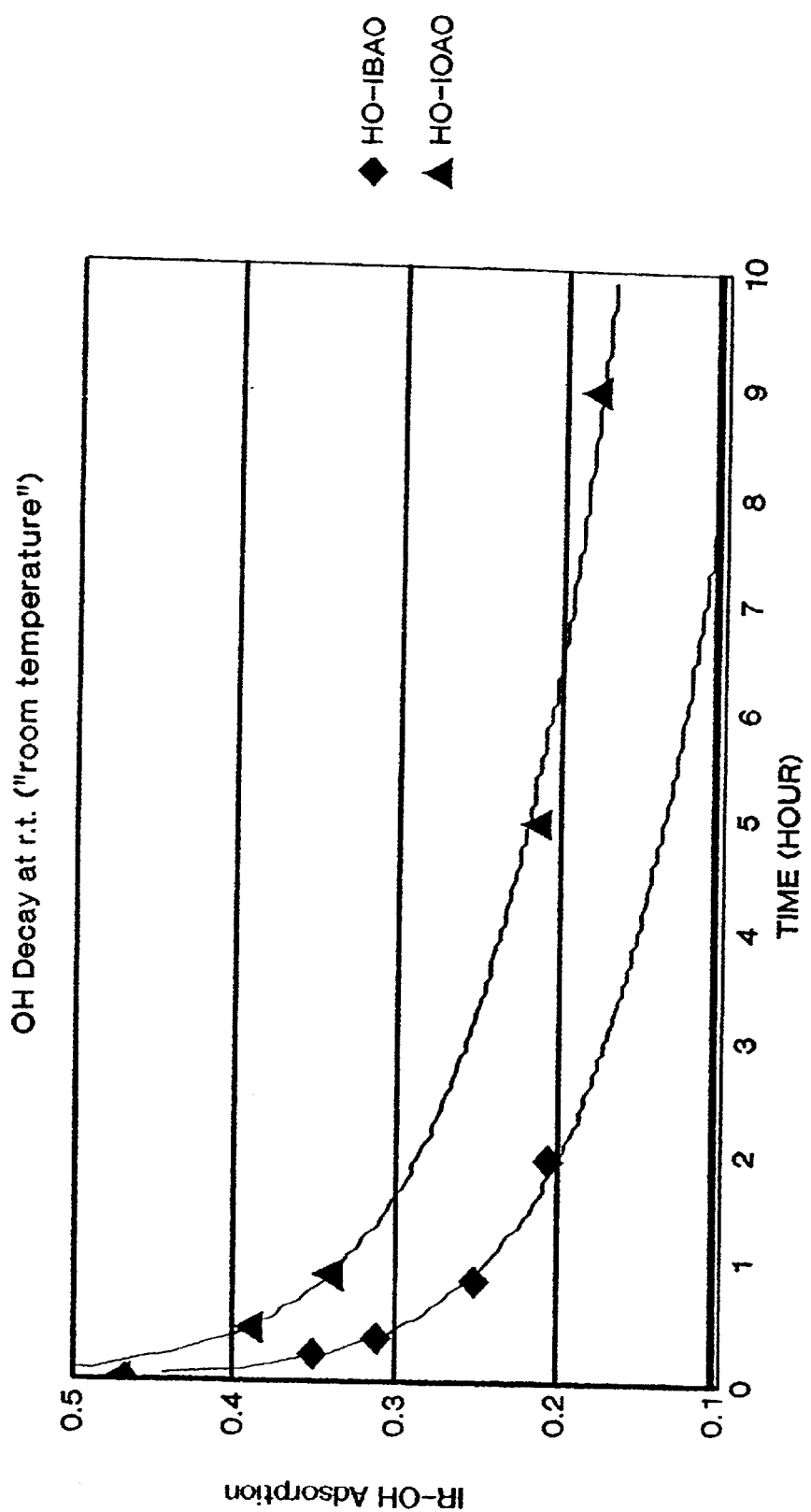
FIG. 6 is a graph illustrating the change in infrared—OH absorption over time at room temperature for HO-IBAO and for hydroxyisooctylaluminoxane (HO-IOAO).
Figure 7:
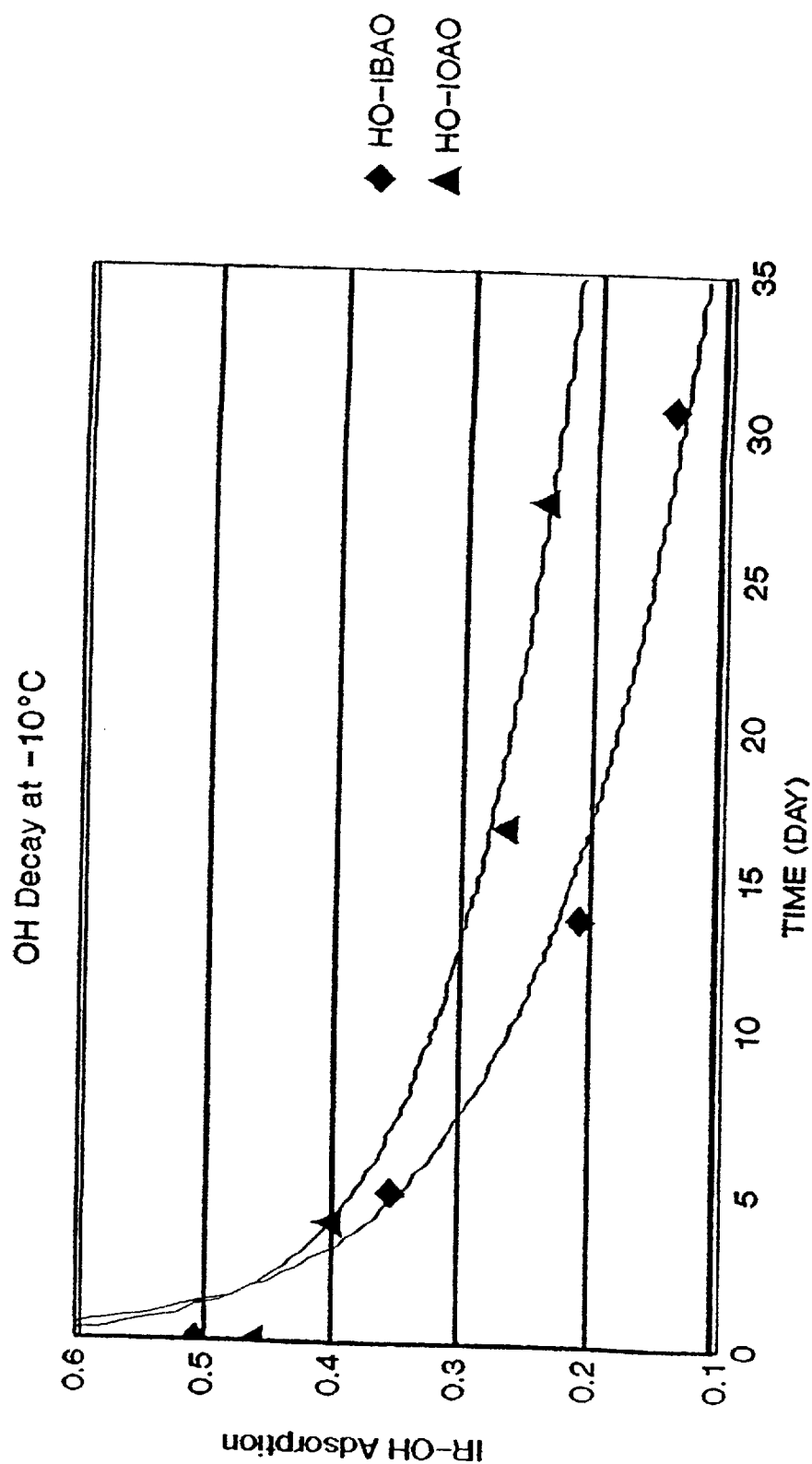
FIG. 7 is a graph illustrating the change in infrared—OH absorption over time at −10° C. for HO-IBAO and for HO-IOAO.

As reference to FIG. 5 shows, this spectroscopy tool is also useful for measuring the effectiveness of a metallocene activator. Thus, a hydroxy-depleted isobutylaluminoxane (aged for three months at ambient temperature, and indicated by IR to contain no detectable amount of hydroxyl groups), hardly reacted with rac-dimethylsilylbis(2-meth-ylindenyl) zirconium dimethyl even at a higher Al/Zr ratio of 50. See FIG. 5, middle. Although the metallocene reacts with the tetraisobutyldialuminoxane (TIBAO) (formed using a water/Al ratio of 0.50 and used at an Al/Zr ratio of 5000), little bathochromic shift occurred, indicating formation of virtually no active catalyst formation. See FIG. 5, bottom. This observation of lack of formation of active catalyst was confirmed by the polymerization run described in Comparative Example G, below.

The following examples (Examples 11–14 and Comparative Examples A–G) illustrate the highly advantageous results achievable using the polymerization reactions of this invention.

EXAMPLE 11

The hydroxy IBAO used in this run had 6.16. wt % Al and had been stored in a freezer at −10° C. in drybox for six days. The IR spectrum showed an absorbance of 0.458 for the 3623 cm$^{-1}$ OH band, which corresponds essentially to an average of 4.2 OH groups per 100 Al atoms.

Polymerization of propylene was carried out in a 2-L stainless steel oil-jacketed reactor which had previously been heated to 100° C. under vacuum for one hour. After the reactor was charged with purified toluene (600 mL) and propylene (400 mL), a 2-mL solution of 1% TIBA in hexane was injected into the reactor and the mixture was stirred at 50° C. for 5 minutes. After that polymerization was initiated by injecting a catalyst solution of rac-dimethylsilylbis(2-methylindenyl)zirconium dimethyl (2 μmol) and hydroxy IBAO(50 μmol, Al/Zr=25) in 3 mL of toluene which had previously been allowed to stand at ambient temperature for one hour. The mixture was stirred at 800 rpm. The temperature immediately began to rise from 50° C. to peak at 74° C. 9 minutes later. No make-up propylene was added. After ten minutes of reaction, the unreacted propylene was quickly vented to stop the polymerization. After adding methanol (>1000 mL), filtering, and drying the solids under vacuum at 100° C. overnight, 101 g of isotactic polypropylene was isolated; polymer properties: M.P. (onset of second melt): 146.3° C.; Melt Flow Index (MFI)(230° C./5 kg): 40.68 (g/10 min); mmmm %: 93.9%; Isotactic Index: 97.3%.

EXAMPLE 12

This polymerization of propylene used an HO-IBAO which was indicated by IR analysis to contain an average of 4.0 OH groups per 100 Al atoms. The materials and procedure were as in Example 11 except that an Al/Zr ratio of 50, and more toluene (800 mL) were used. Yield: 127 g; M.P.(onset of second melt): 144.9° C.; MFI (230° C./5 kg): 87.97 (g/10 min); mmmm %: 93.1%; Isotactic Index: 97.4%.

EXAMPLE 13

This HO-IBAO used in this polymerization was indicated by IR analysis to contain and average of 3.2 OH groups per 100 Al atoms. The materials and procedure were as in Example 11 except that an Al/Zr ratio of 30, and more toluene (800 mL) were used. Yield: 88.6 g.; M.P.(onset of second melt): 146.9° C.; MFI (230° C./5 kg): 56.28 (g/10 min); mmmm %: 93.1%; Isotactic Index: 96.9%; Molecular weight (via GPC): Mw=167,776, Mn=76,772, Mw/Mn= 2.19.

COMPARATIVE EXAMPLE A

The procedure of Example 11 was repeated, except that the catalyst solution was rac-dimethylsilylbis(2-methylindenyl)zirconium dimethyl (1.0 µmol) and conventional methylaluminoxane (MAO) (1.0 mmol, Al/Zr=1000) in toluene, and no TIBA was used as scavenger. Compared to Example 11, this propylene polymerization reaction was much less exothermic, taking a whole hour of reaction for temperature to rise from 50° C. to 81° C.; Yield: 146 g; M.P.(onset of second melt): 144.4° C.; MFI (230° C./5 kg): 79.90 (g/10 min); mmmm %: 92.2%; Isotactic Index: 96.5%; Molecular weight (via GPC): Mw=197,463, Mn=84, 967, Mw/Mn=2.32.

COMPARATIVE EXAMPLE B

This polymerization was carried out in a 300-mL Parr reactor equipped with an internal cooling coil. The reactor in drybox was charged with a catalyst solution of rac-dimethylsilylbis(2-methylindenyl)zirconium dimethyl (0.3 µmol) and MAO (1.5 mmol, Al/Zr=5000) in about 150 mL of dry toluene. The reactor was sealed, transferred, and heated to 68° C. With stirring set at 800 rpm, the polymerization was initiated by pressing in 28 g of liquid propylene. The temperature was maintained at 70° C. by applying cooling intermnittently. After 10 minutes, the polymerization was quenched by adding MeOH. Yield: 7.2 g. M.P. (onset of second melt): 145.9° C.

COMPARATIVE EXAMPLE C

The procedure was as in Example 11 except that the catalyst solution was rac-dimethylsilylbis(2-methylindenyl) zirconium dimethyl (1.0 µmol) and MAO (0.1 mmol, Al/Zr= 100) in toluene. No exothermic reaction was observed. The reaction after one hour produced only a trace of solid polymer.

COMPARATIVE EXAMPLE D

This polymerization used TIBAO (tetraisobutylaluminoxane) made by hydrolyzing TIBA with a half equivalent of water (water to aluminum ratio=0.5) and the IR spectrum of the product showed no evidence of any OH group present. The procedure was as in Example 11 except that an Al/Zr ratio of 100 was used. No polymerization activity was observed.

COMPARATIVE EXAMPLE E

This polymerization was carried out in a 300-mL Parr reactor with procedure analogous to that in Comparative Example D except that the Al/Zr ratio was 5000, reaction temperature was 70° C., and reaction time was 20 minutes. Only 0.91 g of polymer was isolated.

COMPARATIVE EXAMPLE F

This polymerization used hydroxyisobutylaluminoxane indicated by IR analysis to contain an average of 5.3 OH groups per 100 Al atoms. The procedure was as in Example 11 except that an Al/Zr ratio of 3000 was used. The polymerization was initially as exothermic as that in Example 11. However, when the temperature reached 63° C. (from 50° C.) after 4 minutes of reaction, the exothermic reaction suddenly ceased and the temperature quickly reversed its rising trend, returning to 52° C. in the next 6 minutes. The reaction was allowed to continue for an additional 20 minutes. Yield: 38.6 g. M.P.(onset of second melt): 148.0° C.; MFI (230° C./5 kg): 16.67 (g/10 min); mmmm %: 92.6%; Isotactic Index: 96.8%.

COMPARATIVE EXAMPLE G

This polymerization used hydroxyisobutylaluminoxane indicated by IR analysis to contain an average of 3.8 OH groups per 100 Al atoms. The procedure was as in Example 11 except that the metallocene used was rac-dimethylsilylbis (2-methylindenyl)zirconium dichloride not the dimethyl analog. In addition, an Al/Zr ratio of 50, and more toluene (800 mL) were used. No reaction was observed.

EXAMPLE 14

This ethylene polymerization used hydroxyisobutylaluminoxane made by hydrolyzing TIBA with 0.9 equivalent of water. This HO-IBAO was indicated by IR analysis to contain an average of 1.5 OH groups per 100 Al atoms at the time of use. The procedure was as in Example 11 with the following modifications: The catalyst used was a mixture of bis(1-butyl-3-methylcyclopentadienyl)zirconium dimethyl (2 µmol) and hydroxyisobutylaluminoxane (200 µmol), and was allowed to stand at ambient temperature for one hour before being injected. The reactor was charged with 900 mL of dry toluene and pressurized with 300 psig of ethylene, which was fed as needed during polymerization to maintain the pressure. Polyethylene yield: 55.0 g. M.P.(onset of first melt): 131.8° C. The melt flow index (MFI) was too low to be measured. The molecular weight (via GPC) was as follows: Mw=579,652, Mn=243,129, Mw/Mn=2.38.

Examples 15–19 illustrate the preparation, isolation, and storage stability of the isolated catalyst compounds at ambient room temperatures. In these Examples, the stability of the catalyst was monitored by UV-Vis spectroscopy. In this method, it is assumed that the absorbance of the bathochromically shifted metallocenium ion correlates with the catalyst activity; i.e., the higher the absorbance, the more catalytically active the metallocene. This correlation has been verified by Deffieux's research group in three recently published papers: D. Coevoet et al. *Macromol. Chem. Phys.*, 1998, 199, 1451–1457; D. Coevoet et al. *Macromol. Chem. Phys.*, 1998,199, 1459–1464; and J. N. Pedeutour et al. *Macromol. Chem. Phys.*, 1999 199, 1215–1221.

In Example 10 above, it is shown that the starting metallocene having an LMCT band at 394 nm diminishes upon activation by HO-IBAO. The disappearance is accompanied by the growth of a broad absorption band extended just beyond 700 nm. In Examples 15 et seq., use is made of the absorbance at 600 nm for the purpose of monitoring stability. All UV-Vis samples have a same [Zr] concentration of 0.346 mM (2 µmol Zr in 5 g of toluene) in toluene.

EXAMPLE 15

Polymerization Using Rac-ethylenebis(1-indenyl) zirconium Dimethyl Pre-catalyst A 15 ml high pressure mini-reactor was placed in a drybox and equipped with a plastic anchor stirrer rotating at about 500 rpm. Hydroxyisobutylaluminoxane previously was made by hydrolyzing TIBA with one equivalent of water, and at the time of use in this polymerization contained about 4–5 OH groups per 100 Aluminum atoms. The metallocene, rac-ethylenebis(1-indenyl)zirconium dimethyl, was slurried in hexane in the mini-reactor at ambient temperature, and the hydroxyisobutylaluminoxane was added thereto. The metallocene quickly dissolved to give a deep red solution. The Al/Zr molar ratio was 30:1. The mini-reactor was then charged with a portion of the catalyst composition (0.2 micromoles Zr) and a 3 wt % TIBA solution in hexane (about 1 micromole Al). The reactor was then sealed and 6 ml of liquid propylene was pressed into the reactor via a syringe pump to start the polymerization. The temperature was quickly brought to 65° C. within four to six minutes. The polymerization was allowed for another 10 minutes at 65° C., during which time all propylene was consumed. After drying, 3.5 g of polypropylene was collected. The $C_{13}$-nmr of the polymer showed mmmm % equal to 84.5% and isotacticity index of 94.1%.

EXAMPLE 16

Stability of MET-A+HO-IBAO as an Isolated Product (Al/Zr=200)

To a suspension of dimethylsilylbis(2-methylindenyl) zirconium dimethyl (MET-A) (30 mg, 68 $\mu$mol) in 10 mL hexane was added a solution of hydroxyisobutylaluminoxane (HO-IBAO) (13.2 g, 20 mmol Al) with stirring. Prior to the addition, the solution and the suspension were both cooled to –10° C. and after mixing, the resulting mixture was allowed to return to room temperature. The metallocene gradually dissolved to give a deep red-brown solution. After 45 minutes of stirring, the solution was stripped of volatiles under vacuum to initially give a foamy residue which was broken up by a spatula. Another 2 hours of pumping yielded a completely dry brown powder which weighed 1.4 g. The brown solid was stored in a drybox at room temperature, and was periodically sampled for stability determinations. Each sample was redissolved in toluene, and the stability of the product was monitored by UV-Vis at 600 nm by measuring the metallocenium concentration of the respective redissolved samples. Samples were taken right after the isolated product had been dried, and after the isolated product had been stored for 6 days, 15 days, and 39 days. The results, summarized in Table 1, show that the metallocenium concentration stayed constant throughout at least a 39-day period. After one month of storage, the solid product was shown by a micro calorimetric test system to be highly active in ethylene polymerization (50° C./50 psi in toluene).

TABLE 1

Change of UV-Vis Absorbance at 600 nm with Time

| Storage Time | Product of Example 16 |
|---|---|
| Right after drying | 0.183 |
| 6 Days | 0.181 |

TABLE 1-continued

Change of UV-Vis Absorbance at 600 nm with Time

| Storage Time | Product of Example 16 |
|---|---|
| 15 Days | 0.187 |
| 39 Days | 0.182 |

EXAMPLE 17

Stability of MET-A+HO-IBAO Product Dissolved in Toluene

A catalyst solution of Met-A and HO-IBAO with an Al/Zr molar ratio of 100, was prepared. This solution was divided into two solutions, sample A and B, whose UV-Vis spectra upon storage over time were recorded. Sample A was stored at ambient temperature in a drybox at all times. Sample B was stored at ambient temperature for the first 4.5 hours, and after that was stored at –10° C. except during the spectra acquisition which is done at room temperature. The results are summarized in Table 2, in which the values marked with an asterisk are values of samples taken from the product while the product was being stored at –10° C.

TABLE 2

Change of UV-Vis Absorbance at 600 nm with Time

| Storage Time | Sample A | Sample B |
|---|---|---|
| 2 Hours | 0.149 | 0.153 |
| 4.5 Hours | 0.135 | 0.127 |
| 28 Hours | 0.101 | 0.126* |
| 5 Days | 0.081 | 0.124* |
| 12 Days | 0.064 | 0.121* |

The results in Table 2 clearly show that the catalyst is unstable in solution at ambient room temperature but is rather stable in solution at –10° C.

EXAMPLE 18

Stability of MET-A+HO-IBAO as an Isolated Product (Al/Zr=50)

To a solution of HO-IBAO in hexane (6.78 g, 10.2 mmol Al) and 6.1 g toluene was added solid MET-A (88 mg, 204 umol) while the solution was cold. As a consequence of a lower Al/Zr ratio used in this Example, toluene was needed to dissolve the metallocene. After 23 minutes of stirring at room temperature, the resulting dark brown solution was stripped of volatiles in vacuo to give a foamy residue which was broken up by a spatula. After a further 4 hours of pumping, 1.1 g of a brown powder was isolated. The UV-Vis absorbances of this product at 600 nm were 0.116 and 0.120 for solids sampled right after drying and after 6 days of storage at ambient temperature, respectively.

EXAMPLE 19

Stability of MET-A+HO-IBAO as an Isolated Product (Al/Zr=300)

The procedure of Example 17 was followed except that MET-A (100 $\mu$mol) and HO-IBAO in hexane (30 mmol Al) were used and no additional hexane was used. After drying, 3.2 g of a purple-brown solid was isolated. The results of the UV-Vis monitoring are summarized in Table 3.

TABLE 3

Change of UV-Vis Absorbance at 600 nm with Time

| Storage Time | Product of Example 19 |
| --- | --- |
| Right after drying | 0.205 |
| 11 Days | 0.178 |
| 24 Days | 0.177 |

EXAMPLE 20

Stability of MET-A+HO-IBAO as an Isolated Product (Al/Zr=60)

The HO-IBAO used in this Example is more freshly prepared than that in the Example 18. As a consequence, no toluene was needed to dissolve the metallocene. Thus, the procedure in the Example 17 was followed except that MET-A (200 μmol), HO-IBAO in hexane (12 mmol Al), and an additional 4 g of hexane were used. After drying, 1.35 g of a purple-brown solid were isolated. The results of the UV-Vis monitoring are summarized in Table 4.

TABLE 4

Change of UV-Vis Absorbance at 600 nm with Time

| Storage Time | Product of Example 20 |
| --- | --- |
| Right after drying | 0.121 |
| 6 Days | 0.122 |
| 20 Days | 0.132 |

Figure 8:
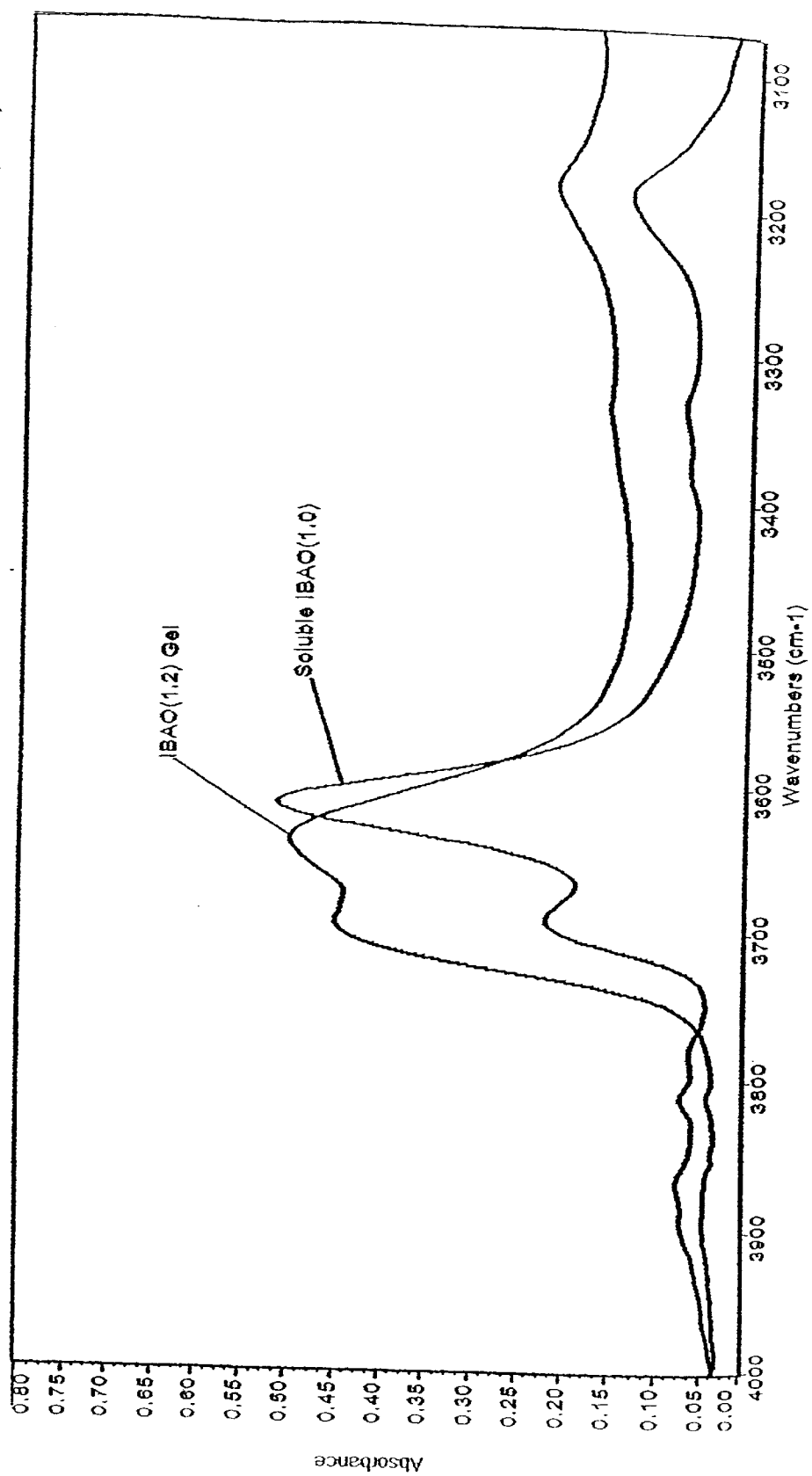
FIG. 8 are superimposed FT-infrared spectra of HO-IBAO (1.2) and soluble HO-IBAO(1.0).
Figure 9:
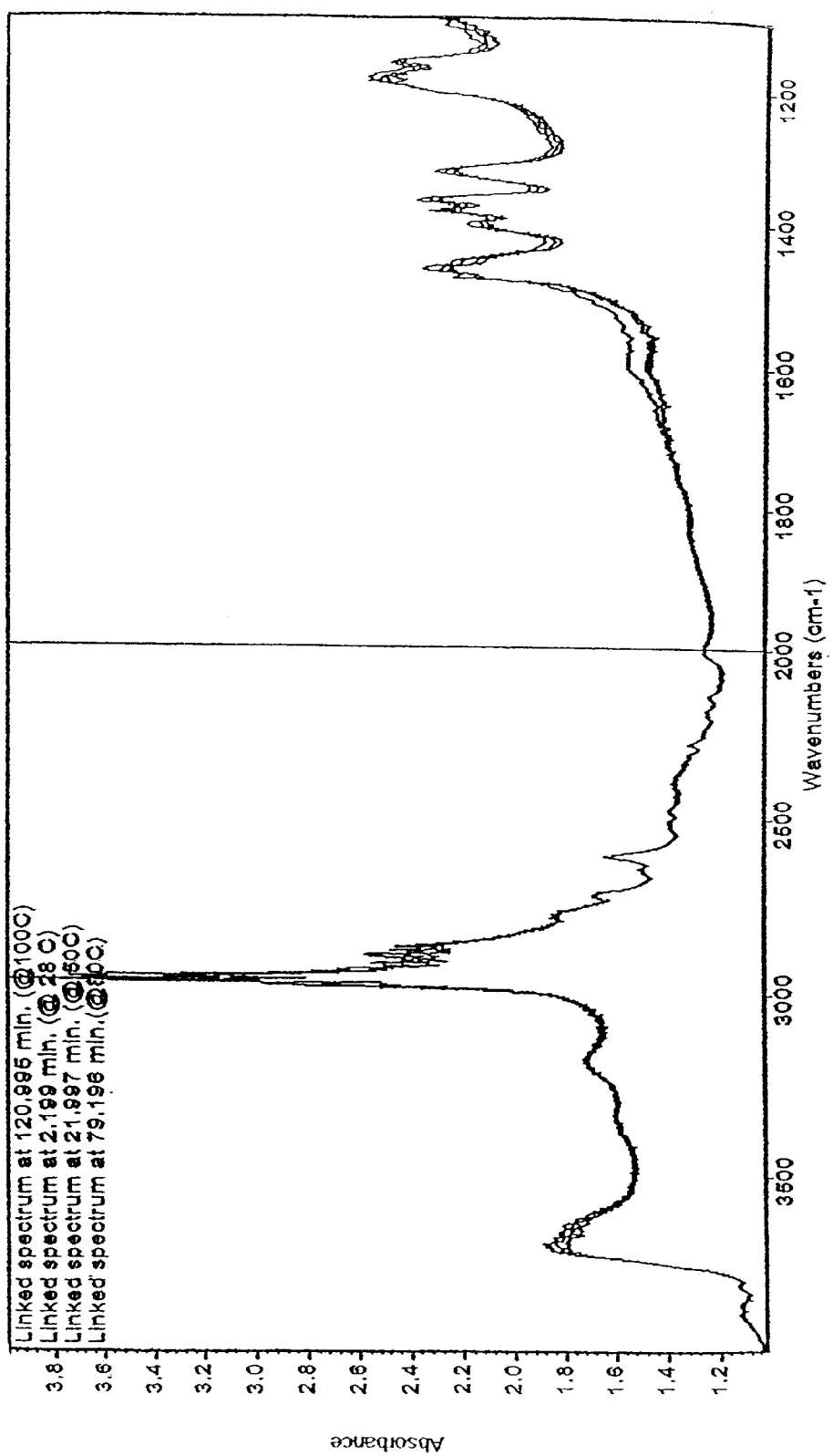
FIG. 9 are variable temperature DRIFTS spectra of HO-IBAO(1.2) gel.

In the following Examples 21–24, it will be seen that one solution for solving the instability problem of the OH groups is by isolating the hydroxyaluminoxane as an insoluble gel or a solid formed from such a gel. Gelation of hydroxyaluminoxane occurs when the water to aluminum molar ratio exceeds a certain amount, which amount is dependent upon the hydroxyaluminoxane involved. In one case, triisobutylaluminum was hydrolyzed with 1.2 equivalents of water. The resulting HO-IBAO(1.2) became an insoluble gel which could be isolated as a solid material after solvent stripping. FIG. 8 shows the FT-IR spectrum in the OH region of the IBAO(1.2) gel (after solvent stripping) overlaid with that of the hexane-soluble IBAO(1.0) for comparison. The IBAO (1.2) gel shown was stored at ambient temperature for a few weeks and still contained no lesser amount of OH groups than in the freshly prepared soluble IBAO(1.0). Furthermore, not only did IBAO(1.2) gel not show the OH-decay at ambient temperature but also the resulting OH groups were remarkably stable even at elevated temperatures. FIG. 9 is a set of four DRIFS (diffuse reflectance infrared fourier transform spectroscopy) spectra of HO-IBAO(1.2) taken at 28° C. (2 min), 50° C. (20 min), 80° C. (57 min), and 100° C. (40 min) with the time spent at each temperature as indicated. It is only at 100° C. that the OH groups start to diminish at a very slow rate. Without being bound to theory, it is believed that this enhanced stability is a result of gelation which allows the OH groups to be immobilized in the polymeric matrix of the gels and, hence, stabilized. It will be appreciated from this disclosure that, like soluble versions of hydroxyaluminoxane, this insoluble gelatinous material, and the solids derived therefrom, contain hydroxyl groups which can be used to activate organometallic compounds via a Brønsted acid mechanism. Unlike soluble aluminoxane, however, the gels and/or the solids derived therefrom serve both as an activator and as a support. This dual role played by the hydroxy aluminoxane gels and/or solid material derived therefrom allows the resulting catalysts to be more stable and to be non-fouling in the polymerization reactor.

EXAMPLE 21

Synthesis of hydroxyisobutylaluminoxane gels

To a TIBA (60.6 g) solution in hexane (193 g) was added water drop wise in two portions. The first portion of water (5.6 g) was added at temp of 0 to −5° C. over one hour, then the solution temp was raised to 25° C., and at that temp another 1.0 g of water was added over 50 minutes. The total amount of water added was 1.19 eq. (water/Al=1.19). During the latter stage of second water addition, some small amount of gel started to form. The solution was put in vacuo to remove hydrolysis by-product, isobutane, and allowed to stir at 15° C. overnight. After 16 hrs of stirring at 15° C., the solution produced lots of gel. Such gelation would continue to a noticeable degree over the next 24 hrs. After that, the amount of gel produced was such that the gel-solution was difficult to pour having very little free-flowing hexanes left.

EXAMPLE 22

Preparation of rac-dimethylsilylbis(2-methylindenyl)zirconium dimethyl catalyst by solid HO-IBAO gels To the gel-solution (12.24 g) produced above (in Example 21) with stirring was added solid rac-dimethylsilylbis(2-methylindenyl)zirconium dimethyl (43 mg). The light yellow metallocene gradually dissolved and turned the gel-solution from colorless to dark brown. After 18 minutes of stirring, the dark brown slurry was stripped of volatiles in vacuo to give a somewhat tacky brown residue, weighing 1.8 g. When this material was used in a bulk propylene polymerization, the catalyst activity was quite high but severe reactor fouling occurred. To avoid fouling, the soluble portion of the tacky brown residue was removed by washing consecutively by hexane (15 ml) and toluene (25 ml) and filtered. The toluene slurry was difficult to filter, so the colored supernatant was decanted. The resulting brown material was pumped to dryness to give now a non-tacky solid, weighing 1.18 g. The ICP analysis of this solid showed 30.0 wt % Al and 0.43 wt % Zr.

EXAMPLE 23

Propylene Polymerization

Polymerization of propylene was carried out in a 4-liter reactor charged with 2200 ml of liquid propylene. At 65° C. with vigorous stirring, 1.0 ml of 5% TIBA (as scavenger) was injected into the reactor first, which was quickly followed by another injection of the catalyst from Example 22 (110 mg slurried in 2 ml of dry hexane) to initiate polymerization. After one hour of reaction, the unreacted propylene was quickly vented. After drying, 153 g of irregular shaped granulates having 78%>2000 microns were collected. No reactor fouling was seen. Polymer properties: bulk density: 0.26 g/cc; M.P.: 142.42/148.97° C. (onset of second melt/peak); MFI (230° C./5 kg): 39.93 g/10 min.

EXAMPLE 24

In example 23, the catalyst gel solids were apparently too big, which resulted in a very large polymer particle size and reduced catalyst activity. Therefore, the same brown solid catalyst was ground to finer particles using a mortar/pestle. Repeating the polymerization using the resulting finer particles (67.2 mg) for one hour produced 222 g of polymer. Thus, simply by grinding the catalyst particles, the catalyst productivity was improved from 1391 g/g/h in polymerization-1 to 3304 g/g/h in polymerization-2. Again, there was no reactor fouling. Polymer properties: bulk density=0.27 g/cc; M.P.=142.33/148.66° C. (onset of second melt/peak); molecular weight data (via GPC): Mw=256,000, Mn=131,000, Mw/Mn=1.95.

While this invention has been specifically illustrated by reactions between a metallocene and a hydroxyaluminoxane, it is to be understood that other suitable organometallic reactants having an appropriate leaving group can be employed. For example it is contemplated that the organometallic complexes described in the following publications will form ionic compounds of this invention, provided that at least one of the halogen atoms bonded to the d-block or f-block metal atom is replaced by a suitable leaving group such as a methyl, benzyl, or trimethylsilylmethyl group:

Small, B. L.; Brookhart, M.; Bennett, A, M. A. *J. Am. Chem. Soc.* 1998, 120, 4049.

Small, B. L.; Brookhart, M. *J. Am. Chem. Soc.* 1998, 120 7143.

Johnson, L. K.; Killian, C. M.; Brookhart, M. *J. Am. Chem. Soc.* 1995, 117,6414.

Killian, C. M.; Johnson, L. K.; Brookhart, M. *Organometallics* 1997, 16, 2005.

Killian, C. M.; Tempel, D. J.; Johnson, L. K.; Brookhart, M. *J. Am. Chem. Soc.* 1996, 118, 11664.

Johnson, L. K.; Mecking, S.; Brookhart, M. *J. Am. Chem. Soc.* 1996, 118, 267.

It will now be appreciated that this invention is susceptible to considerable variation in its practice, as the invention provides numerous advantages and features. Some of these advantages and features can be expressed in terms of the various embodiments of the invention itself. The following comprises non-limiting examples of such embodiments.

A1. A gelatinous composition of matter formed by bringing together at least (i) a hydroxyaluminoxane in an inert solvent and (ii) a treating agent, such that the gelatinous composition has a reduced OH-decay rate as compared to the OH-decay rate of the hydroxyaluminoxane.

A2. A composition according to A1 wherein the treating agent is comprised of water.

A3. A composition according to A2 wherein the composition is substantially insoluble in an inert organic solvent.

A4. A composition according to A3 wherein the hydroxyaluminoxane has less than 25 OH groups per 100 aluminum atoms.

A5. A composition according to A4 wherein the hydroxyaluminoxane has no more than 15 OH groups per 100 aluminum atoms.

A6. A composition according to A3 wherein the hydroxyaluminoxane consists essentially of hydroxyisobutylaluminoxane.

A7. A composition according to any of A1, A2, A3, A4, A5, or A6 wherein the OH-decay rate of said composition is reduced relative to the OH-decay rate of said hydroxyaluminoxane by a factor of at least 5.

A8. A solid composition of matter formed by removing at least some of said inert solvent from the gelatinous composition of matter which is in accordance with any of A1, A2, A3, A4, A5, or A6, said solid composition of matter being characterized by having a reduced OH-decay rate as compared to the OH-decay rate of the hydroxyaluminoxane.

B1. A gelantinous composition comprised of hydroxyaluminoxane and characterized by having an OH-decay rate which is reduced as compared to the OH-decay rate of the hydroxyaluminoxane in a liquid form.

B2. A composition according to B1 wherein said hydroxyaluminoxane has less than 25 hydroxyl groups per 100 aluminum atoms.

B3. A composition according to B1 wherein said hydroxyaluminoxane has less than 15 hydroxyl groups per 100 aluminum atoms.

B4. A composition according to B1 wherein said hydroxyaluminoxane consists essentially of hydroxyisobutylaluminoxane.

B5. A composition according to B1 wherein the OH-decay rate of said composition is reduced, as compared to that of said hydroxyaluminoxane in unsupported form, by a factor of at least 5.

B6. A composition according to B5 wherein said hydroxyaluminoxane has less than 25 hydroxyl groups per 100 aluminum atoms.

B7. A composition according to B5 wherein said hydroxyaluminoxane has less than 15 hydroxyl groups per 100 aluminum atoms.

B8. A composition according to B5 wherein said hydroxyaluminoxane consists essentially of hydroxyisobutylaluminoxane.

C1. A process comprising converting a hydroxyaluminoxane into a gelatinous composition of matter by bringing together (i) said hydroxyaluminoxane in an inert solvent and (ii) a treating agent compatible with said hydroxyaluminoxane, whereby the rate of OH-decay for said composition of matter is reduced relative to the rate of OH-decay of (i).

C2. A process according to C1 wherein said treating agent is comprised of water.

C3. A process according to C1 wherein said hydroxyaluminoxane of (i) has less than 25 OH groups per 100 aluminum atoms.

C4. A process according to C1 wherein said hydroxyaluminoxane of (i) has less than 15 OH groups per 100 aluminum atoms.

C5. A process according to C1 wherein said hydroxyaluminoxane of (i) consists essentially of hydroxyisobutylaluminoxane.

C6. A process according to C1 wherein said composition of matter is substantially insoluble in an inert organic solvent.

C7. A process according to C1 wherein the OH-decay rate of said composition is reduced, as compared to the OH-decay rate of (i), by a factor of at least 5.

C8. A process according to C7 wherein said treating agent is comprised of water.

C9. A process according to C7 wherein said hydroxyaluminoxane of (i) has less than 25 OH groups per 100 aluminum atoms.

C10. A process according to C7 wherein said hydroxyaluminoxane of (i) has less than 15 OH groups per 100 aluminum atoms.

C11. A process according to C7 wherein said hydroxyaluminoxane of (i) consists essentially of hydroxyisobutylaluminoxane.

C12. A process according to C7 wherein said composition of matter is substantially insoluble in an inert organic solvent.

D1. An activated catalyst composition formed by bringing together (A) a gelantinous composition of matter, or a solid composition of matter formed therefrom, or both, the gelatinous composition of matter being formed by bringing together at least (i) a hydroxyaluminoxane in an inert solvent and (ii) a treating agent compatible with said hydroxyaluminoxane, said gelantinous composition of (A) having a reduced OH-decay rate relative to the OH-decay rate of (i); and (B) a d- or f-block metal compound having at least one leaving group on a metal atom thereof.

D2. A catalyst composition according to claim D1 wherein said d- or f-block metal compound is a Group 4 metal.

D3. A catalyst composition according to claim D1 wherein said d- or f-block metal compound is a metallocene.

D4. A catalyst composition according to claim D3 wherein the d- or f-block metal of said metallocene is at least one Group 4 metal.

D5. A catalyst composition according to claim D3 wherein said metallocene contains two bridged or unbridged cyclopentadienyl-moiety-containing groups.

D6. A catalyst composition according to claim D5 wherein the Group 4 metal of said metallocene is zirconium.

D7. A catalyst composition according to claim D5 wherein the Group 4 metal of said metallocene is titanium.

D8. A catalyst composition according to claim D5 wherein the Group 4 metal of said metallocene is hafnium.

D9. A catalyst composition according to any of D1, D2, D3, D4, D5, D6, D7, or D8 wherein said hydroxyaluminoxane of (i) has less than 25 hydroxyl groups per 100 aluminum atoms.

D10. A catalyst composition according to any of D1, D2, D3, D4, D5, D6, D7, or D8 wherein said hydroxyaluminoxane of (i) consists essentially of hydroxyisobutylaluminoxane.

D11. A catalyst composition according to any of D1, D2, D3, D4, D5, D6, D7, or D8 wherein said composition in a dry or substantially dry state is able to be maintained at a temperature in the range of about 10 to about 60° C. for a period of at least 48 hours without losing fifty percent (50%) or more of its catalytic activity.

E1. A process of preparing an activated olefin polymerization catalyst composition, which process comprises bringing together (A) a gelantinous composition of matter, or a solid composition of matter formed therefrom, or both, the gelatinous composition of matter being formed by bringing together (i) a hydroxyaluminoxane in an inert solvent and (ii) a treating agent compatible with said hydroxyaluminoxane, whereby the rate of OH-decay for said composition is reduced relative to the rate of OH-decay of (i); and (B) a d- or f-block metal compound having at least one leaving group on a metal atom thereof.

E2. A process according to E1 wherein (A) and (B) are brought together in an inert diluent.

E3. A process according to E1 wherein (A) and (B) are brought together in the absence of an inert diluent.

E4. A process according to E1 wherein said hydroxyaluminoxane of (i) consists essentially of hydroxyisobutylaluminoxane.

E5. A process according to E1 wherein said hydroxyaluminoxane of (i) has less than 25 hydroxyl groups per 100 aluminum atoms.

E6. A process according to E1 wherein said hydroxyaluminoxane of (i) has less than 15 hydroxyl groups per 100 aluminum atoms.

E7. A process according to E1 wherein said d- or f-block metal compound is a metallocene.

E8. A process according to E7 wherein said at least one leaving group of said metallocene is a methyl group.

E9. A process according to E7 wherein said metallocene contains two bridged or unbridged cyclopentadienyl-moiety-containing groups.

E10. A process according to E9 wherein the metal of said metallocene is a Group 4 metal.

E11. A process according to E10 wherein said Group 4 metal is zirconium.

E12. A process according to E10 wherein said Group 4 metal is titanium.

E13. A process according to E10 wherein said Group 4 metal is hafnium.

E14. A process according to any of E1, E2, E3, E4, E5, E6, E7, E8, E9, E10, E11, E12, or E13 wherein said activated catalyst composition is recovered and maintained at a temperature in the range of about 10 to about 60° C. for a period of at least 48 hours without losing fifty percent (50%) or more of its catalytic activity.

F1. An olefin polymerization process which comprises bringing together in a polymerization reactor or reaction zone (1) at least one polymerizable olefin and (2) an activated catalyst composition which is in accordance with any of D1, D2, D3, D4, D5, D6, D7, D8, D9, or D10.

F2. An olefin polymerization process according to F1 wherein the polymerization process is conducted as a gas-phase polymerization process.

F3. An olefin polymerization process according to F1 wherein the polymerization process is conducted in a liquid phase diluent.

F4. An olefin polymerization process according to F1 wherein the polymerization process is conducted as a fluidized bed process.

F5. An olefin polymerization process according to F1 wherein said hydroxyaluminoxane of (i) has less than 25 hydroxyl groups per 100 aluminum atoms.

F6. An olefin polymerization process according to F5 wherein the polymerization process is conducted as a gas-phase polymerization process.

F7. An olefin polymerization process according to F5 wherein the polymerization process is conducted in a liquid phase diluent.

F8. An olefin polymerization process according to F5 wherein the polymerization process is conducted as a fluidized bed process.

F9. An olefin polymerization process according to F1 wherein said hydroxyaluminoxane of (i) consists essentially of hydroxyisobutylaluminoxane.

G1. A process which comprises bringing together (i) an aluminum alkyl in an inert solvent and (ii) a water source, under hydroxyaluminoxane-forming reaction conditions and using an amount of (ii) sufficient to cause a gelatinous composition of matter to form.

G2. A process according to G1 wherein said aluminum alkyl is a trialkylaluminum.

G3. A process according to G1 wherein said water source consists essentially of free water.

G4. A process according to G1 wherein said aluminum alkyl is triisobutylaluminum, said water source is free water, and said amount of (ii) provides at least about 1.1 molar equivalents of oxygen in (ii) to aluminum in (i).

G5. A process according to G1 further comprising bringing together said gelatinous composition of matter and a d- or f-block metal compound having at least one leaving group on a metal atom thereof, so as to form an activated polymerization catalyst.

G6. A process according to G5 wherein said d- or f-block metal compound is a metallocene.

G7. A process according to G6 wherein said at least one leaving group of said metallocene is a methyl group.

G8. A process according to G6 wherein said metallocene contains two bridged or unbridged cyclopentadienyl-moiety-containing groups.

G9. A process according to G8 wherein the metal of said metallocene is a Group 4 metal.

G10. A process according to G9 wherein said Group 4 metal is zirconium.

G11. A process according to G9 wherein said Group 4 metal is titanium.

G12. A process according to G9 wherein said Group 4 metal is hafnium.

G13. A process according to G1 further comprising removing solvent from said gelatinous composition of matter so as to form a solid composition of matter, and then bringing together said solid composition of matter and a d- or f-block metal compound having at least one leaving group on a metal atom thereof, so as to form an activated polymerization catalyst.

G14. A process according to G13 wherein said d- or f-block metal compound is a metallocene.

G15. A process according to G14 wherein said at least one leaving group of said metallocene is a methyl group.

G16. A process according to G14 wherein said metallocene contains two bridged or unbridged cyclopentadienyl-moiety-containing groups.

G17. A process according to G16 wherein the metal of said metallocene is a Group 4 metal.

G18. A process according to G17 wherein said Group 4 metal is zirconium.

G19. A process according to G17 wherein said Group 4 metal is titanium.

G20. A process according to G17 wherein said Group 4 metal is hafnium.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, solvation, ionization, or other transformation during the course of contacting, blending or mixing operations, if done in accordance with the disclosure hereof and with the use of ordinary skill of a chemist and common sense, is within the purview and scope of this invention.

Each and every patent or other publication referred to in any portion of this specification is incorporated in full into this disclosure by reference, as if fully set forth herein.

The foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A gelatinous composition formed by bringing together at least (i) a hydroxyaluminoxane in an inert solvent and (ii) a treating agent which is able to form a gelatinous composition when mixed with said hydroxyaluminoxane, wherein the gelatinous composition has a lower OH-decay rate as compared to the OH-decay rate of the hydroxyaluminoxane.

2. A composition according to claim 1 wherein the treating agent is comprised of water.

3. A composition according to claim 2 wherein the composition is substantially insoluble in the inert organic solvent.

4. A composition according to claim 3 wherein the hydroxyaluminoxane has less than 25 OH groups per 100 aluminum atoms.

5. A composition according to claim 4 wherein the hydroxyaluminoxane has no more than 15 OH groups per 100 aluminum atoms.

6. A composition according to claim 3 wherein the hydroxyaluminoxane consists essentially of hydroxyisobutylaluminoxane.

7. A composition according to any of claims 1, 2, or 4 wherein the OH-decay rate of said composition is lower than the OH-decay rate of said hydroxyaluminoxane by a factor of at least 5.

8. A solid composition formed by removing at least some of said inert solvent from a gelatinous composition which is in accordance with any of claims 1, 2, 3, 4, 5, or 6, said solid composition being characterized by having a lower, OH-decay rate as compared to the OH-decay rate of the hydroxyaluminoxane.

9. A gelatinous composition comprised of hydroxyaluminoxane and characterized by having an OH-decay rate which is lower than the OH-decay rate of the hydroxyaluminoxane in a liquid form.

10. A composition according to claim 9 wherein said hydroxyaluminoxane in liquid form has less than 25 hydroxyl groups per 100 aluminum atoms.

11. A composition according to claim 9 wherein said hydroxyaluminoxane in liquid form has less than 15 hydroxyl groups per 100 aluminum atoms.

12. A composition according to claim 9 wherein said hydroxyaluminoxane in liquid form consists essentially of hydroxyisobutylaluminoxane.

13. A process comprising converting a hydroxyaluminoxane into a gelatinous composition by bringing together at least (i) a hydroxyaluminoxane, (ii) a treating agent which is able to form a gelatinous composition when mixed with said hydroxyaluminoxane, and (iii) an inert solvent which optionally is or includes a solvent in which (i) was dissolved when used in conducting the process, whereby the rate of OH-decay for said composition is reduced relative to the rate of OH-decay of (i) in undissolved form or in the form of a solution in said inert solvent.

14. A process according to claim 13 wherein said treating agent is comprised of water.

15. A process according to claim 13 wherein said hydroxyaluminoxane of (i) has less than 25 OH groups per 100 aluminum atoms.

16. A process according to claim 13 wherein said hydroxyaluminoxane of (i) has less than 15 OH groups per 100 aluminum atoms.

17. A process according to claim 13 wherein said hydroxyaluminoxane of (i) consists essentially of hydroxyisobutylaluminoxane.

18. A process according to claim 13 wherein said composition is substantially insoluble in n-hexane at 25° C.

19. A process according to claim 13 wherein the OH-decay rate of said composition is lower than the OH-decay rate of (i), by a factor of at least 5.

* * * * *